(12) United States Patent
Plumas et al.

(10) Patent No.: US 9,783,782 B2
(45) Date of Patent: Oct. 10, 2017

(54) PLASMACYTOID DENDRITIC CELL LINE USED IN ACTIVE OR ADOPTIVE CELL THERAPY

(75) Inventors: Joel Plumas, Grenoble (FR); Caroline Aspord, La Tronche (FR); Laurence Chaperot-Dubonnet, Francin (FR)

(73) Assignee: ETABLISSEMENT FRANCAIS DU SANG, La Plaine Saint Denis (FR)

( * ) Notice: Subject to any disclaimer, the term of this patent is extended or adjusted under 35 U.S.C. 154(b) by 533 days.

(21) Appl. No.: 12/993,076

(22) PCT Filed: May 15, 2009

(86) PCT No.: PCT/EP2009/055909
§ 371 (c)(1),
(2), (4) Date: Feb. 28, 2011

(87) PCT Pub. No.: WO2009/138489
PCT Pub. Date: Nov. 19, 2009

(65) Prior Publication Data
US 2012/0020998 A1 Jan. 26, 2012

(30) Foreign Application Priority Data
May 16, 2008 (FR) ...................... 08 02659

(51) Int. Cl.
*A61K 39/21* (2006.01)
*C12N 5/0784* (2010.01)
*A61K 35/12* (2015.01)
*A61K 39/00* (2006.01)

(52) U.S. Cl.
CPC ...... *C12N 5/0639* (2013.01); *A61K 2035/124* (2013.01); *A61K 2039/5154* (2013.01); *A61K 2039/5158* (2013.01)

(58) Field of Classification Search
None
See application file for complete search history.

(56) References Cited

U.S. PATENT DOCUMENTS

| 7,341,870 B2 * | 3/2008 | Plumas et al. ............... 435/325 |
| 2003/0032050 A1 * | 2/2003 | Berzofsky et al. ............ 435/6 |
| 2004/0265998 A1 | 12/2004 | Goletz et al. |

FOREIGN PATENT DOCUMENTS

FR 2848565 12/2004

OTHER PUBLICATIONS

Angel et al. (Vaccine 2007, vol. 25, p. 3913-3921).*
Celluzzi et al. (J. Exp. Med. 1996).*
Santegoets et al., (Cancer Immunology, Immunotherapy, 2006, p. 1480-1490).*
Yee et al., (PNAS, 2002, p. 16168-16173).*
Chaperot L. et al: "Identification of a leukemic counterpart of the plasmacytoid dendritic cells" Blood American Society of Hematology, US, vol. 97, No. 10, May 15, 2001, pp. 3210-3217, XP002243855.
Chaperot L. et al.: "Leukemic plasmacytoid dendritic cells share phenotypic and functional features with their normal counterparts" European Journal of Immunology, vol. 34, No. 2, Feb. 2004, pp. 418-426, XP002505517.
Plumas J. et al.: "Plasmacytoid dendritic cells capture and cross-present viral antigens from influenza virus infected cells" Bulletin du Cancer, Editions Scientifiques Elsevier, Paris, FR, vol. 95, No. sp. iss. Si, Mar. 1, 2008, p. S32, XP009109113.
S.J.A.M. Santegoets et al.: "Invitro priming of tumor-specific cytotoxic T lymphocytes using allogeneic dendritic cells derived from the human MUTZ-3 cell line" Cancer Immunology. Immunotherapy, Springer, Berlin, DE, vol. 55, No. 12, Feb. 9, 2006, pp. 1480-1490, XP0192422502.
Yee C. et al.: "Adoptive T cell therapy using antigen-specific CD8+ T cell clones for treatment of patients with metastatic melanoma: In vivo persistence, migration, and antitumor effect of transferred T cells." Proceedings of the National Academy of Sciences of the United States of America, vol. 99, No. 25, Dec. 10, 2002, XP002505178.
International Search Report; PCT/EP2009/055909; dated Aug. 11, 2009.
Banchereau et al., "Dendritic Cells as Therapeutic Vaccines Against Cancer" vol. 5, (2005), pp. 296-306.
Di Pucchio et al., "Direct Prosteasome-independent Cross-presentation of Viral Antigen by Plasmacytoid Dendritic Cells on Major Histocompatibility Complex Class I" Nat Immunol, 9(5), May 2008, pp. 551-557.
Guckel et al., "A CD80-transfected Human Breast Cancer Cell Variant Includes HER-2/neu-specific T Cells in HLA-A*02-matched Situations in vitro as well as in vivo" 54, (2005), pp. 129-140.
Hartmann et al., Identification and Functional Analysis of Tumor-infiltrating Plasmacytoid Dendritic Cells in Head and Neck Cancer Cancer Research, 63, (2003), pp. 6478-6487.
Hoeffel et al., "Antigen Crosspresentation by Human Plasmacytoid Dendritic Cells" Immunity, 27, (2007), pp. 481-492.
Holtl et al., "Allogeneic Dendritic Cell Vaccination Against Metastatic Renal Cell Carcinoma With or Without Cyclophosphamide" Cancer Immunol Immunother 54, (2005), 663-670.
Hus et al., "Allogeneic Dendritic Cells Pulsed with Tumor Lysates or Apoptotic Bodies as Immunotherapy for Patients with Early-Stage B-Cell Chronic Lymphocytic Leukemia" Leukemia, 19, (2005), pp. 1621-1627.
Palucka et al., "Boosting Vaccinations with Peptide-Pulsed CD34+ Progenitor-Derived Dendritic Cells Can Expand Long-Lived Melanoma Peptide-Specific CD8+ T Cells in Patients with Metastatic Melanoma" J. Immunother, 25, (2005), pp. 158-168.

(Continued)

*Primary Examiner* — Agnieszka Boesen
(74) *Attorney, Agent, or Firm* — Cantor Colburn LLP

(57) ABSTRACT

The present invention relates to a method for inducing and amplifying specific effectors, which comprises obtaining pulsed plasmacytoid dendritic cells (pDC) by incubation of a pDC line with at least one antigen, the pulsed pDC being subsequently irradiated and brought into contact with peripheral blood mononuclear cells (PBMC), and cultured or injected into an organism. The pulsed and irradiated pDC and the PBMC share at least one major histocompatibility complex (MHC) allele.

21 Claims, 18 Drawing Sheets

(56) References Cited

OTHER PUBLICATIONS

Perrot et al., "Dendritic Cells Infiltrating Human Non-Small Cell Lunch Cancer are Blocked at Immature Stage" The Journal of Immunology, 178, (2007), pp. 2763-2769.
Thurner et al., "Vaccination wiht Mage-3A1 Peptide-pulsed Mature, Monocyte-derived Dendritic Cells Expands Specific Cytotoxic T Cells and Induces Regression of Some Metastases in Advanced Stage IV Melanoma" J. Exp. Med. vol. 190, No. 11, Dec. 6, 1999, pp. 1669-1678.
Treilleux et al., "Dendritic Cell Infiltration and Prognosis of Early Stage Breast Cancer" Clinical Cancer Research, 10, (2004), pp. 7466-7474.
Angel et al., "Virosome-mediated Delivery of Tumor Antigen to Plasmacytoid Dendritic Cells" Vaccine; 25; (2007); pp. 3919-3921.
Asprod et al., "A Novel Cancer Vaccine Strategy Based on HLA-A*0201 Matched Allogeneic Plasmacytoid Dendritic Cells" pDC-Based Cancer Vaccine; vol. 5; Issue: 5; (May 2010); 16 Pages.
Bendriss-Vermare et al., "In situ Leukemic Plasmacytoid Dendritic Cell Pattern of Chemokine Receptors Expression and in vitro Migratory Response", Lukemia; (2004); pp. 1-8.
Bendriss-Vermare et al., "Virus Overrides the Propensity of Human CD40L-Activated Plasmacytoid Dendritic Cells to Produce Th2 Mediators Through Synergistic Induction of IFN-y and Th1 Chemokine Production", Journal of Leukocyte Biology; vol. 78; (2005); pp. 954-966.
Blum et al., "Mechanisms of TRAIL-induced Apoptosis in Leukemic Plasmacytoid Dendritic Cells", Experimental Hematology; 34; (2006); pp. 1655-1662.
Briere et al., "Origin and Filiation of Human Plasmacytoid Dendritic Cells", Human Immunology; 63; (2002); pp. 1081-1093.
Chaperot et al., "Identification of a Leukemic Counterpart of the Plasmacytoid Dendritic Cells", Blood, vol. 97; May 18, 2001; pp. 3210-3217.
Chaperot et al., "Leukemic Plasmacytoid Dendritic Cells Share Phenotypic and Functional Features With Their Normal Counterparts", Eur. J. Immunol.; 34; (2004); pp. 418-426.
Chaperot et al., "Virus or TLR Agonists Induce TRAIL-Mediated Cytotoxic Activity of Plasmacytoid Dendritic Cells", The Journal of Immunology; (2006); 176; pp. 248-255.
Feuillard et al., "Clinical and Biologic Features of CD4+ CD56+ Malignancies", Blood; vol. 99; No. 5; (Mar. 1, 2012); pp. 1556-1563. (Including cover page).
Garnache-Ottou et al., "Expression of the Myeloid-associated Marker CD33 is not an Exclusive Factor for Leukemic Plasmacytoid Dendritic Cells", Blood; vol. 105; No. 3; (Feb. 1, 2005); pp. 1256-1264.
Jacob et al., "CD4+ CD56+ Lineage Negative Maligancies: A New Entity Developed From Malignant Early Plasmacytoid Dendritic Cells", Journal of Hematology; vol. 88(08); (2003); pp. 941-955).
Villadangos et al., "Antigen-Presentation Properties of Plasmacytoid Dendritic Cells", Immunity; 29; (Sep. 19, 2008); pp. 352-361.
Aspord, C., et al., "A Novel Cancer Vaccine Strategy Based on HLA-A*0201 Matched Allogeneic Plasmacytoid Dendritic Cells" PLoS ONE (2010) vol. 5(5), 16 pages.
Wikipedia, [online]; retrived on Nov. 7, 2016, retrived from the Internet, https://en.wikipedia.org/w/index.php?title=Cell_culture&oldid=747399571, "Cell Culture", Wikipedia, The Free Encyclopedia, 14 pages.

* cited by examiner

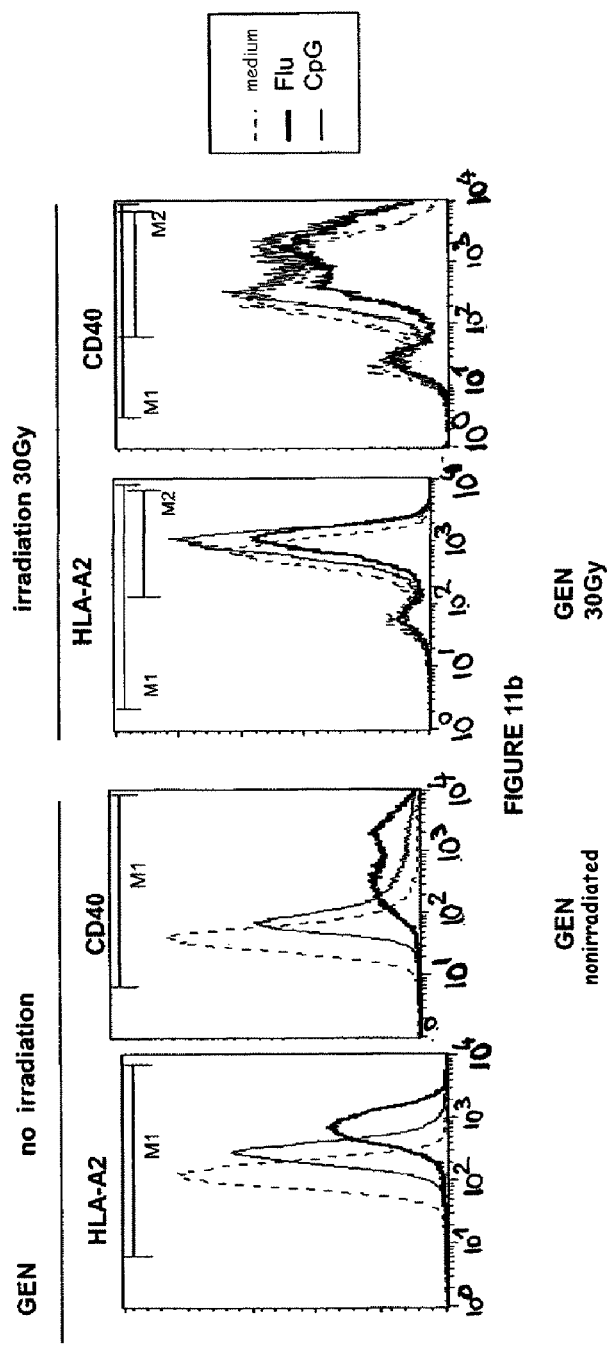
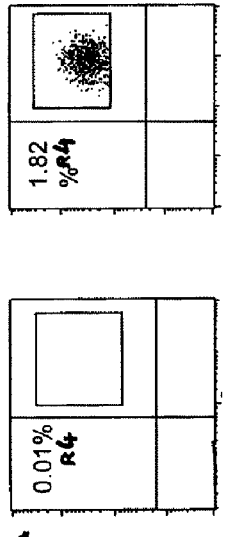
FIGURE 11b
FIGURE 11c

PLASMACYTOID DENDRITIC CELL LINE USED IN ACTIVE OR ADOPTIVE CELL THERAPY

The present invention relates to a method for inducing and amplifying cytotoxic effectors using a plasmacytoid dendritic cell (pDC) line in a semi-allogenic context. The invention also relates to the use of a pDC line for obtaining a medicament for use in the treatment and/or prevention of infectious diseases or cancers. The invention also relates to a vaccine comprising pDCs and a method for treating cancers or infectious diseases.

Dendritic Cells

Dendritic cells are key players in the immune response: they are responsible for the uptake of antigens and the processing of said antigens for the purpose of the presentation thereof to T lymphocytes. There are various types of dendritic cells, which can be distinguished by their ontogeny and their functional capacities: myeloid dendritic cells (mDCs) derived from precursors expressing CD11c, CD13 and CD33 molecules, and plasmacytoid dendritic cells (pDCs), characterized by a very strong expression of the IL3 receptor (CD123) and capable of maturing under the effect of IL3 and of CD40L, or in the presence of a virus.

pDCs were identified specifically from tonsils in 1997 by G. Grouard et al. (Grouard G et al., J Exp Med., 1997; 185:1101-1111); they have also been described in the blood (O'Doherty U. et al., Immunology, 1994; 82: 487-493; Robinson SP. et al., Eur J. Immunol. 1999; 29: 2769-2778), in the lymph nodes (Cella M. et al., Nat Med., 1999; 5: 919-923) and in the thymus (Res PC. et al., Blood, 1999; 94: 2647-2657; Bendriss-Vermare N. et al., J Clin Invest., 2001; 107: 835-844). These cells are characterized by their plasmacytoid-type morphology and their phenotype.

pDCs express CD4, HLA-DR and CD45RA molecules and are devoid of the myeloid markers CD11c and CD13 (Cella M. et al., Nat Med., 1999; 5: 919-923), or of line-specific markers such as CD3, CD14 and CD19, although expression of CD2, CD5 or CD7 has sometimes been observed (Cella M. et al., Nat Med., 1999; 5: 919-923; Res PC. et al., Blood., 1999; 94: 2647-2657). More recently, it has been possible to identify the lectin BDCA2 specifically expressed by pDCs; BDCA4 is found on pDCs but is also present on monocyte-derived DCs (Dzionek A. et al., J. Immunol., 2000; 165: 6037-6046). An argument in favor of the idea that these cells belong to the lymphoid line is the fact that they express mRNA encoding preTalpha chains (Res PC. et al., Blood., 1999; 94: 2647-2657), lambda like 14.1 and SpiB (Bendriss-Vermare N. et al., J Clin Invest., 2001; 107: 835-844). These cells express the IL-3 receptor very strongly and the GM-CSF receptor weakly (Cella M. et al., Nat Med., 1999; 5: 919-923; Rissoan MC. et al., Science., 1999; 283: 1183-1186), and these two cytokines promote the survival of pDCs (Grouard G. et al., J Exp Med., 1997; 185: 1101-1111; Kohrgruber N. et al., J. Immunol., 1999; 163: 3250-3259; Robinson SP. et al., Eur J. Immunol., 1999; 29: 2769-2778) which otherwise die very rapidly in vitro. The costimulating molecules CD80 and CD86 are absent or weakly expressed (Grouard G. et al., J Exp Med., 1997; 185: 1101-1111), and, at the immature stage, these cells are not capable of activating T lymphocytes (Kohrgruber N. et al., J. Immunol., 1999; 163: 3250-3259). On the other hand, in the presence of IL-3, of CD40L or of a virus, the pDCs mature, strongly express antigen presentation accessory molecules (CD40, CD80, CD86 and HLA-DR) and then become capable of activating the proliferation of allogenic T cells (Kohrgruber N. et al., J. Immunol., 1999; 163: 3250-3259; Grabbe S. et al., Immunol Today., 2000; 21: 431-433; Kadowaki N. et al., J Exp Med., 2000; 192: 219-226). Depending on the stimulus responsible for their maturation (IL3 or virus), pDCs will polarize the response of the naïve T lymphocytes that they activate, more or less strictly, toward a Th1 or Th2 profile (Rissoan MC. et al., Science., 1999; 283: 1183-1186; Cella M. et al., Nat. Immunol., 2000; 1: 305-310; Kadowaki N. et al., J Exp Med., 2000; 192: 219-226). pDCs are also described for inducing regulatory CD8 and CD4 T responses (Gilliet & Liu, Hum. Immunol. 63, 2002; Wei et al., Cancer Res. 65(12), 2005; Gilliet & Liu, J. Exp. Med., 195(6), 2002).

Dendritic Cells in a Tumoral or Infectious Context

In a tumoral context, pDCs often exhibit an immature state and tolerogenic functions (Perrot et al., The J. of Imm., 2007; Hartmann et al., Cancer Res., 63, 2003; Treilleux et al., Clinical Cancer Res., 10, 2004). It should be noted that the infiltration of breast cancer by pDCs is correlated with an unfavorable patient survival prognosis, suggesting a contribution in the progression of said cancer (Treilleux et al., 2004), or an inhibition of their functions in the context of the tumor microenvironment.

In the context of viral infections, pDCs have a central role in initiating the antiviral response, by virtue of their secretion of interferon-alpha, and owing to their ability to present viral antigens, in order to activate cytotoxic CD8+ T lymphocytes (Hoefel et al., 2008, Immunity 27: 481-492; Di Pucchio, 2008, Nature Immunol. adv online publication).

Active Immunotherapy and Allogenic Immunotherapy

Many clinical trials demonstrate the ability of autologous myeloid dendritic cells (mDCs) to stimulate antitumor immune responses (Thurner et al., 1999, J. Exp. Med. 190(11): 1669-78; Palucka et al., 2005, J. Immunother. 28(2): 158-68). In most of these trials, the mDCs are generated from monocytes taken from the patient, and cultured in the presence of cytokines for several days, and this sometimes involves an additional step of cell maturation. The production of these mDCs must therefore be carried out for each patient individually, and the clinical trials carried out up until now with autologous mDCs do not provide sufficient clinical efficacy to improve overall patient survival (Banchereau et al., 2005, Nat. Rev. Immunol. 5(4): 296-306).

The immunogenicity of cell vaccines could be improved in an allogenic context; thus, the use of semi-allogenic mDCs or of semi-allogenic tumor lines in immunotherapy protocols is already documented (Hus et al., 2005, Leukemia 19: 1621-1627; Holtl et al., 2005, Cancer Immunol Immunother. 54: 663-670). mDCs can be obtained from the MUTZ3 line, which is a CD34+ myeloid cell line derived from a leukemia. The obtaining of mDCs from this cell line is complex (stimulation with GM-CSF, IL-4 and TNF-α, then maturation by adding TNF-α, IL-6, IL-1β and PGE2). These MUTZ-3-derived mDCs are described as being able to induce tumor antigen-specific cytotoxic T cells in vitro (Santegoets et al., 2006 Cancer Immunol. Immunother. 55: 1480-1490, US 2004/0265998). However, the level of induction of the response remains very low, with only 0.4% of antigen-specific cytotoxic T lymphocytes being obtained among the T lymphocytes.

Moreover, the KS breast cancer line transfected with the CD80 costimulator molecule can also induce tumor antigen-specific T cells (Guckel, 2005, Cancer Immunol. Immunother., 54: 129-140) and is already being used in phase I/II clinical trials. However, the response induced is restricted with respect to antigens expressed by this line (Her-2/Neu)

and does not make it possible to induce responses against other tumor or viral antigens.

The present invention provides solutions to the problems of the current immunotherapy strategies, related to the difficulty in implementing the protocols and the industrialization thereof, to the lack of therapeutic efficacy and to the fact that the strategies are developed for a highly targeted pathological condition and therefore have a very restricted field of application.

Specifically, the subject of the present invention is a method for inducing and amplifying specific effectors using a pDC line in a semi-allogenic context, the use of said line for producing a medicament, in particular a vaccine, and also a method for preventing and/or treating cancers and/or infectious diseases.

DESCRIPTION OF THE INVENTION

The present invention relates to a method for inducing and amplifying specific effectors in vitro, which comprises obtaining pulsed plasmacytoid dendritic cells (pDCs) by incubation of a pDC line with at least one antigen, the pulsed pDCs being subsequently irradiated and brought into contact with peripheral blood mononuclear cells (PBMCs), and cultured. The pulsed and irradiated pDCs and the PBMCs share at least one major histocompatibility complex (MHC) allele.

A greater amplification of the number of specific effectors can be obtained by means of at least one further round of bringing the cells derived from the abovementioned culturing into contact with pulsed and irradiated pDCs, followed by a culturing step.

The present invention also relates to a method for inducing and amplifying specific effectors, which comprises obtaining pulsed plasmacytoid dendritic cells (pDCs) by incubation of a pDC line with at least one antigen, the pulsed pDCs being subsequently irradiated, said pulsed and irradiated pDCs being injected into an organism. The pDCs share at least one MHC allele with the PBMCs of the organism into which they are injected. The injection of pulsed and irradiated pDCs can be repeated.

In the context of the present invention, the term "organism" defines most particularly humans or humanized mice.

The term "cell line" applies to mammalian cells cultured in vitro. Primary mammalian cells do not multiply in culture, or stop multiplying in culture after a limited number of divisions. The cell lines according to the present invention are capable of multiplying indefinitely, something of which primary or secondary cultures of mammalian cells are incapable. These properties of the human plasmacytoid dendritic cell (pDC) lines according to the invention make it possible to advantageously obtain large amounts of cells by multiplication or proliferation of these cells in vitro.

In one embodiment of the invention, the pDC line is obtained from pDC leukemia cells. European patent EP 1 572 989 B1 describes a method for obtaining and culturing pDC cell lines from cells of these leukemias. This patent describes most particularly the human pDC line, called GEN2.2, deposited with the CNCM (Collection Nationale de Cultures de Microorganismes [French National Collection of Microorganism Cultures], Institut Pasteur, 25 rue du Docteur Roux, F-75015 Paris) on Sep. 24, 2002, under the number CNCM I-2938 according to Rule 6.1 of the Treaty of Budapest, and the human plasmacytoid dendritic cell line, called GEN3, deposited with the CNCM on Oct. 16, 2003, under the number CNCM I-3110 according to Rule 6.1 of the Treaty of Budapest. These lines can be used in an entirely preferred implementation of the invention.

The term "pulsed" signifies that the pDC cells (line) are incubated with an antigen.

In the context of the present invention, the term "antigen" defines a molecule recognized by cells of the immune system and capable of triggering a cell-mediated immune reaction.

The antigens according to the present invention may be natural or modified, tumor or microbial (in particular bacterial or viral) antigens, such as peptides, proteins, glycopeptides, glycoproteins or phosphorylated proteins.

The antigens can be introduced into the pDC line culture medium or can be expressed by the pDC line transfected with a vector which allows the expression of said antigen.

In one preferred embodiment of the invention, the antigens are peptides which can be obtained from antigenic proteins of tumor or viral origin.

In one particular embodiment of the invention, the peptides which can be obtained from tumor antigens can be chosen from the peptides included in the sequence of the antigens CEA, NY-BR1, Her-2/Neu, PSA, RAGE-1, PRAME, TRP-2, MAGE-A1, MAGE-A2, MAGE-A4, MAGE-A9, MAGE-A10, MAGE-C2, MUC-1, p53, hTERT, survivin, melan-A/MART-1 (SEQ ID No. 1), GP100 (SEQ ID No. 2), tyrosinase (SEQ ID No. 3), MAGE-A3 (SEQ ID No. 4) or NY-ESO1 (SEQ ID No. 5), which are modified or unmodified.

In another embodiment of the invention, the peptides which can be obtained from viral antigens can be chosen from the peptides included in the sequence of the antigens env, nef, gp41, gp120, gag (SEQ ID No. 6) or pol (SEQ ID No. 7) of the HIV virus, HBc or HBs of the HBV virus, core, NS3 or NS5 of the HCV virus, Flu M1 (SEQ ID No. 8) of the influenza virus, CMVpp65 (SEQ ID No. 9) of the CMV virus, BMLF1 (SEQ ID No. 10), LMP2 (SEQ ID No. 11), EBNA-2 (SEQ ID No. 12) or EBNA-3a (SEQ ID No. 13) of the EBV virus, which are modified or unmodified.

In the context of the present invention, the term "specific effector" applies to the immunity cells capable of recognizing a specific antigen or a product derived from this antigen.

In one particular embodiment of the invention, the specific effectors are cytotoxic effectors and, most particularly, these cytotoxic effectors are T lymphocytes which are specific for the antigen used, and in particular CD8+.

The subject of the present invention is also the use of a pDC line for producing a medicament for the prevention and/or treatment of infectious diseases or cancers. Thus, the subject of the present invention is also: a pharmaceutical or nonpharmaceutical composition comprising a pulsed and irradiated pDC line, a composition comprising a culture of cells, said culture comprising a pulsed and irradiated pDC line and also PBMCs, said pDCs and PBMCs sharing at least one major histocompatibility complex (HMC) allele, but also a composition comprising specific effectors which can be obtained by means of the method for inducing and amplifying specific effectors as described above.

Said line may be provided in the form of a kit, which also comprises PBMCs, the pDCs and the PBMCs sharing at least one MHC allele. In one particular form, the kit can also comprise at least one antigen.

The subject of the invention is also a vaccine, characterized in that it comprises a pulsed and irradiated pDC line as agent for activating the immune system, it being possible for said vaccine to be administered in the context of a method of vaccination.

According to another aspect, the subject of the invention is a method for preventing and/or treating cancers and/or infectious diseases, characterized in that an irradiated and pulsed pDC line is injected into an organism, the PBMCs of said organism and the pDCs sharing at least one major histocompatibility complex (MHC) allele.

According to yet another aspect, the subject of the invention is a method for preventing and/or treating cancers and/or infectious diseases, characterized in that the specific effectors obtained by incubation of a pDC line with at least one antigen, the pulsed pDCs being subsequently irradiated and brought into contact with PBMCs, and cultured, are injected, the pDCs and the PBMCs sharing at least one major histocompatibility complex (MHC) allele.

Among the infectious diseases, mention may be made of diseases of which the agent is a microorganism such as a bacterium, a fungus, a yeast or alternatively a virus, and more particularly infections due to the influenza virus (for example: flu), the HIV virus (for example: AIDS), CMV (cytomegalovirus), EBV (Epstein Barr virus; for example: mononucleosis), HBV and HCV (for example: hepatitis), and diseases due to emergent viruses.

Among the cancers which may be treated prophylactically or therapeutically, mention may be made of melanoma, breast cancer, lung cancer or else prostate cancer, and virus-induced cancers.

The invention will be described in terms of some of its aspects in detail in the following examples.

Flow cytometry analysis of the percentage of specific CD8+ T cells on day (D) 0 and on D7 of the culture of PBMCs, derived from healthy donors, with the pDC line GEN2.2 pulsed with a peptide (respectively, viral peptide CMV pp 65 and tumor peptide MelA) using tetramers. The percentages indicated correspond to the percentages of tetramer+ cells among the CD8+ T cells.

Figure 2:
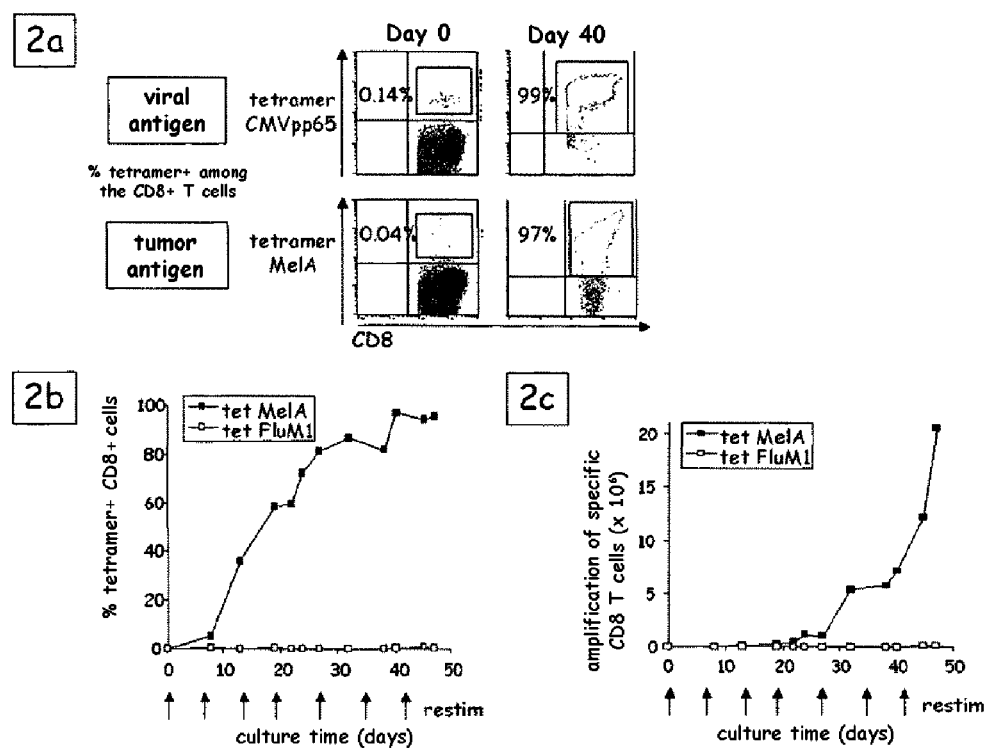

FIG. 2: Efficacy of repeated stimulations for amplifying specific CD8 T cells

2a) Flow cytometry analysis of CD8+ T cells at D0 and D40 of the culture of PBMCs, derived from healthy donors, with the pDC line GEN2.2 pulsed with the CMVpp65 or MelA peptides after weekly stimulations in the presence of IL-2. The percentages indicated correspond to the percentages of tetramer+ cells among the CD8+ T cells.

2b) Change in the percentage of tetramer+ CD8+ T cells, and

2c) Amplification ($\times 10^6$) of the absolute number of MelA-specific CD8 T cells after weekly stimulation of PBMCs with the pDCs pulsed with MelA, in the presence of IL-2 (the FluM1 tetramer is shown as a control). The arrows indicate the restimulations carried out (restim).

Figure 3:
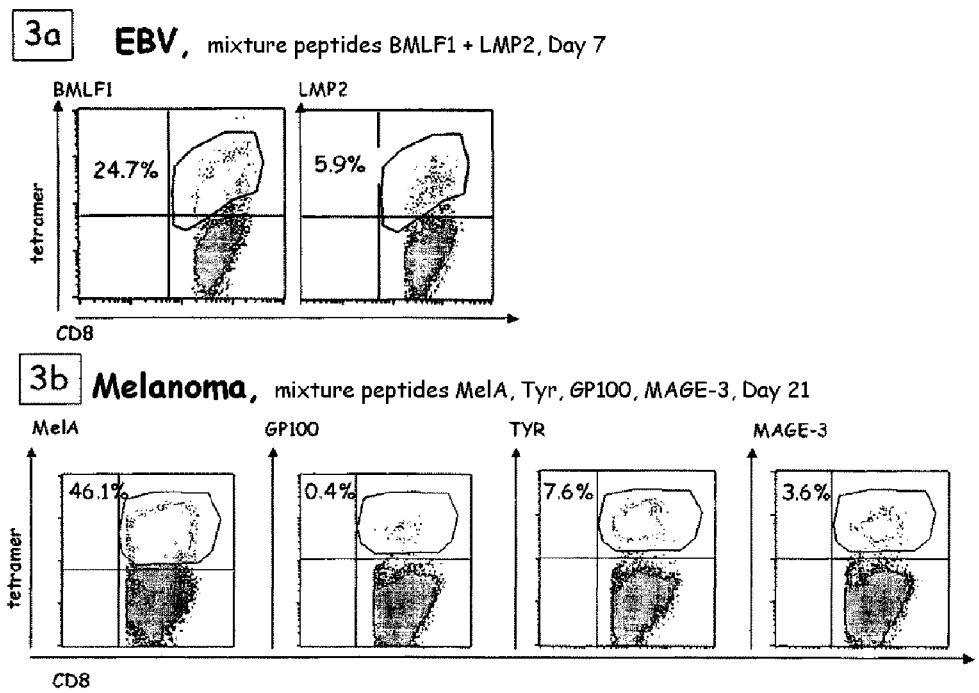

FIG. 3: Simultaneous induction of multispecific CD8 T responses

Flow cytometry analysis of the specificity of the CD8+ T cells on D7 (3a) or on D21 (3b) of the culture of PBMCs, derived from healthy donors, with the pDC line GEN2.2 pulsed with a mixture of various peptides derived from viral antigens (derived from the EBV virus: BMLF1 and LMP2, FIG. 3a) or tumor antigens (melanoma: MelA, GP100, TYR, MAGE-3, FIG. 3b). The percentages indicated correspond to the percentages of tetramer+ cells among the CD8+ T cells.

Figure 4:
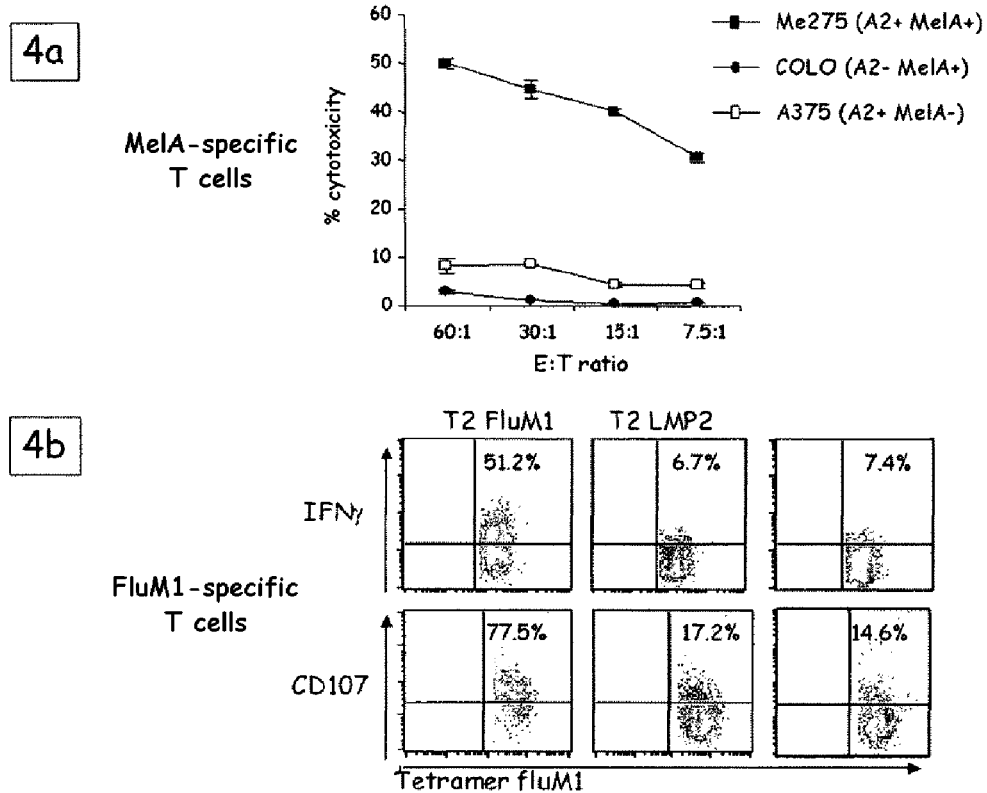

FIG. 4: The specific CD8 T cells generated are functional in vitro in an HLA- and antigen-restricted manner 4a) Antigen-restriction and HLA-A2-restriction of the cytotoxic activity of the MelA-specific CD8 T cells generated by culturing PBMCs (HLA-A2 donor) with the pulsed and irradiated GEN2.2 pDC line, with respect to melanoma lines: the Me275 and A375 lines are HLA-A2, the Me275 and COLO lines express the MelA antigen.

4b) Secretion of IFNγ and surface expression of CD107 by the FluM1-specific CD8 T cells generated by the pulsed and irradiated GEN2.2 pDC line after restimulation (left and center panels) or no restimulation (right panel; −) on T2 cells pulsed with the FluM1 peptide or a control peptide (LMP2); effector/target (E/T) ratio=10/1.

Figure 5:
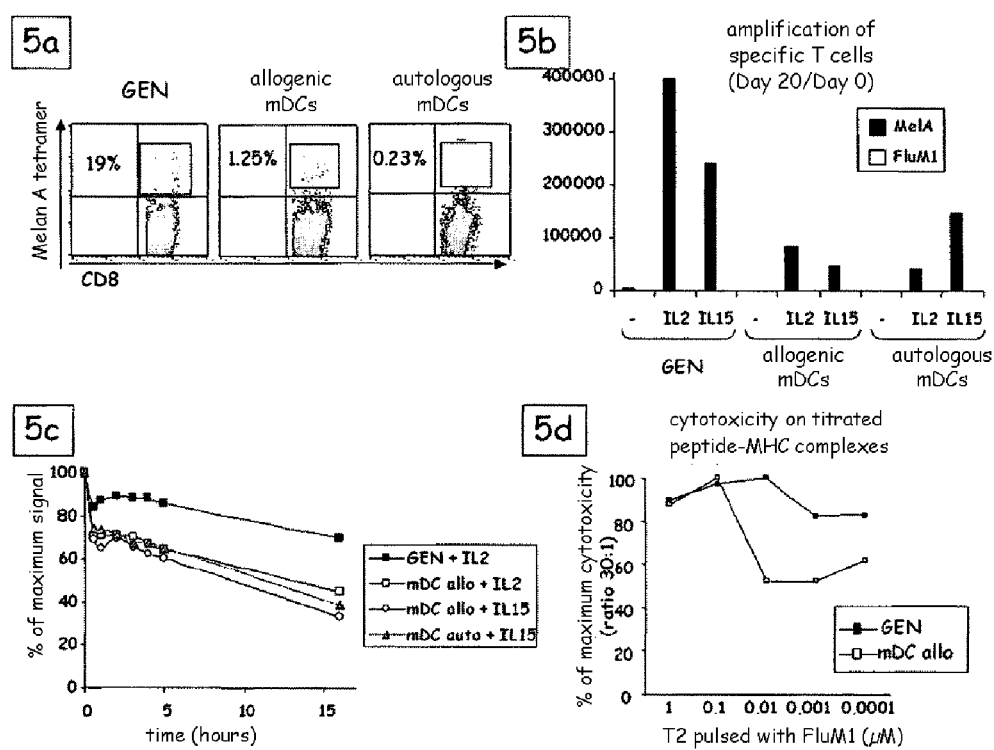

FIG. 5: Comparison of the pulsed and irradiated pDC line according to the invention with allogenic or autologous myeloid DCs with respect to inducing high-affinity and high-avidity specific CD8 T cells 5a) Flow cytometry analysis of the CD8+ T cells on D20 of the culture of PBMCs, derived from healthy donors, with, respectively, the pDC line GEN2.2 (GEN), or allogenic or autologous mDCs pulsed with the MelA peptide, after weekly stimulations in the absence of cytokines. The percentages indicated correspond to the percentages of tetramer+ cells among the CD8+ T cells.

5b) Amplification of the absolute number of MelA-specific CD8+ T cells on D20 of the culture of PBMCs, derived from healthy donors, with, respectively, the pDC line GEN2.2 (GEN), or allogenic or autologous mDCs pulsed with the MelA peptide, after weekly stimulations in the absence (−) or in the presence of the IL-2 or IL-15 cytokines.

5c) Comparison of the affinity of the specific CD8 T cells generated, respectively, with the pDC line (GEN2.2), or allogenic (mDC allo) or autologous (mDC auto) mDCs, measured by the dissociation of the tetramer as a function of the time after labeling.

5d) Comparison of the avidity of the specific CD8 T cells generated, respectively, with the pDC line GEN2.2 (GEN) or allogenic mDCs (mDC allo), measured by their cytotoxic activity with respect to the T2 cells pulsed with decreasing concentrations of peptide. The results of c and d are expressed as a percentage of the maximum signal obtained (maximum labeling with the tetramer and maximum cytotoxicity, respectively).

Figure 6:
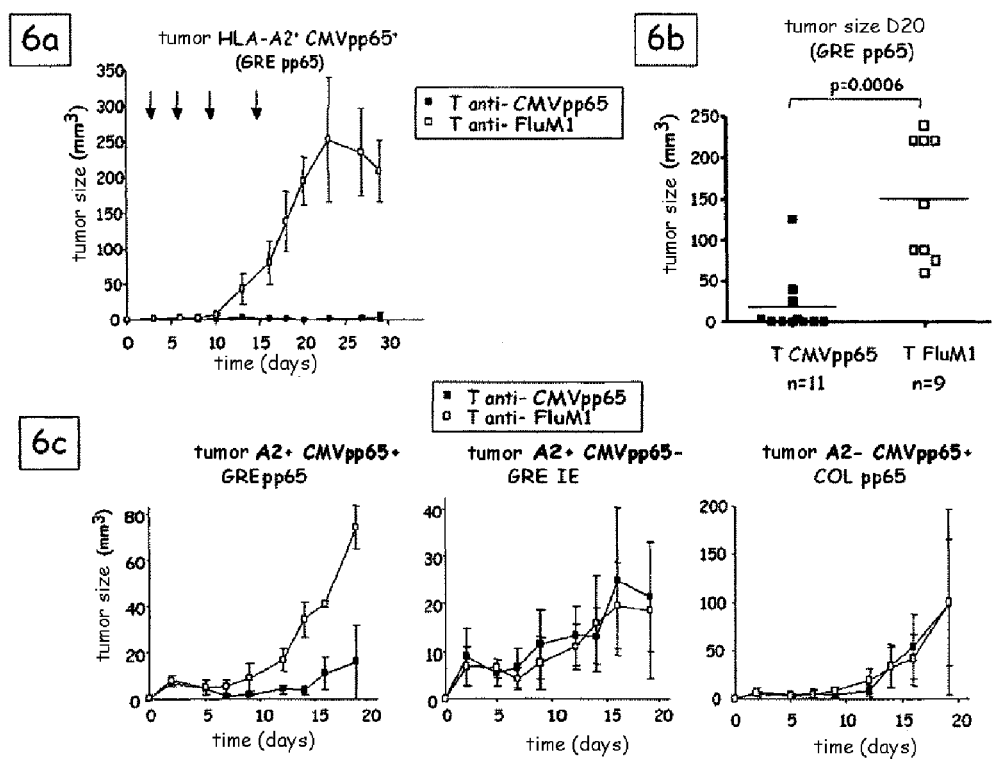

FIG. 6: The specific CD8 T cells generated by the pulsed pDC line according to the invention are functional in vivo 6a) Progression of the tumor growth of HLA-A2+ and CMVpp65+ human lines implanted in NOD-SCID $b2m^{-/-}$ immunodeficient mice after intratumor adoptive transfer of CMVpp65-specific or FluM1-specific CD8 T cells amplified by the pulsed and irradiated GEN2.2 pDC line using PBMCs from an HLA-A2+ donor. A representative experiment is shown. The arrows indicate the injections of specific T cells.

6b) Comparison of tumor size 20 days after tumor implantation. Each point represents one humanized mouse.

6c) Antigen restriction and HLA restriction of the therapeutic efficacy of specific CD8 T cells generated by the pulsed irradiated pDC line according to the invention after adoptive transfer of said T cells. Progression of tumor growth of HLA-A2+ or HLA-A2− human lines expressing or not expressing the CMVpp65+ antigen, implanted in NOD-SCID $b2 m^{-/-}$ immunodeficient mice, after intratumor adoptive transfer of CMVpp65-specific or FluM1-specific CD8 T cells amplified by the pulsed and irradiated pDC line according to the invention using the PBMCs from an HLA-A2 donor.

Figure 7:
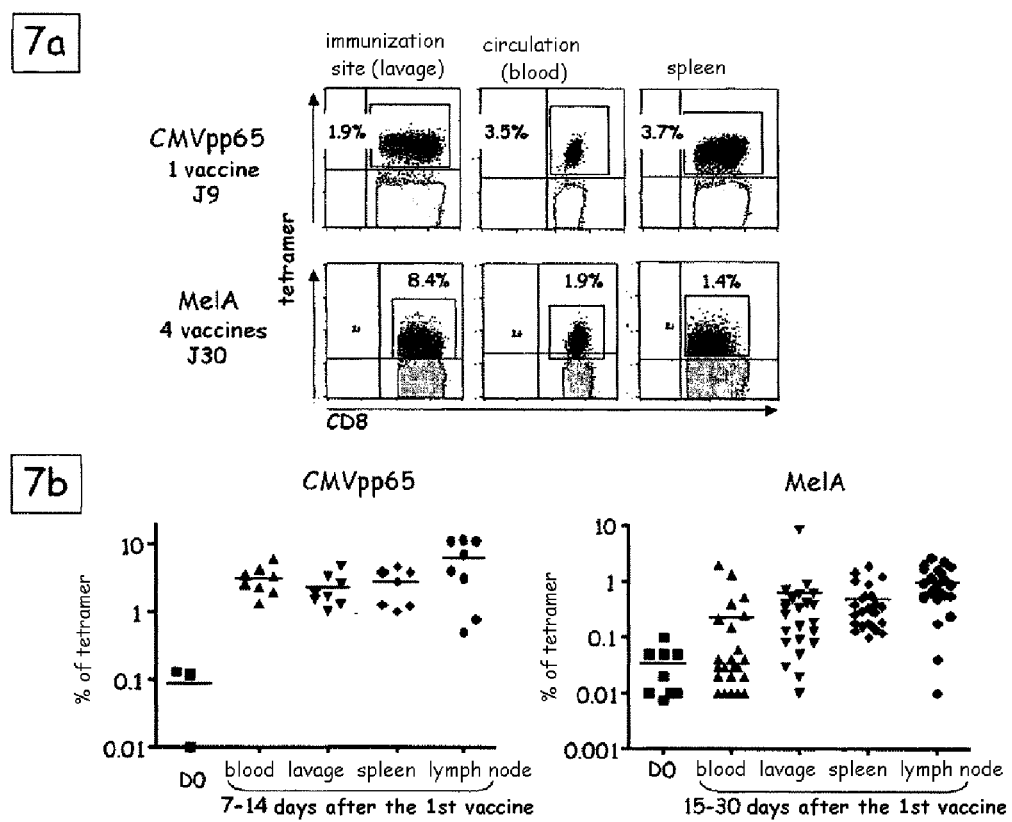

FIG. 7: Response to vaccination with the pulsed and irradiated pDC line according to the invention in a model of humanized mice 7a) NOD-SCID b2m$^{-/-}$ immunodeficient mice were reconstituted intraperitoneally with human HLA-A2 PBMCs and vaccinated one a week with the pulsed and irradiated pDC line according to the invention, also intraperitoneally. The graphs show the tetramer+ CD8+ T cells at the site of vaccination (immunization site (lavage)), in the circulation (blood) and in the lymphoid organs (spleen) of the animals vaccinated with the pDC line pulsed with the CMVpp65 or MelA peptides, respectively, 9 (D9) and 30 days (D30) after the first vaccine. The percentages indicated correspond to the percentages of tetramer+ cells among the CD8+ T cells.

7b) Percentages of specific CD8+ T cells before (D0) and after vaccination with the pDC line pulsed with the CMVpp65 or MelA peptides and irradiated (after 1 vaccine and 3 boosters) in various organs of the humanized mice. Each point represents one humanized mouse.

Figure 8:
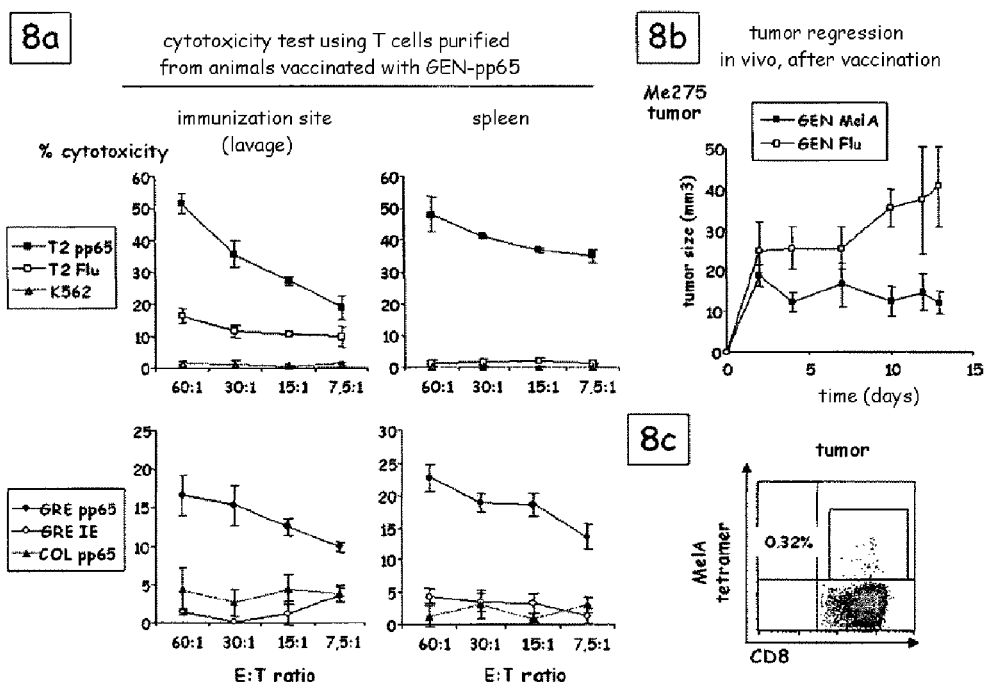

FIG. 8: Therapeutic efficacy of the CD8 T cells generated after vaccination with the pulsed and irradiated pDC line according to the invention in a model of humanized mice 8a) Ex-vivo cytotoxic activity of CD8 T cells purified from the peritoneal lavage (left panels) and from the spleen (right panels) of humanized mice vaccinated with the GEN2.2 line, pulsed with the CMVpp65 peptide (GEN-pp 65) and then irradiated, with respect to T2 cells pulsed with the CMVpp65 peptide or an irrelevant peptide (upper panels) and with respect to HLA-A2+ or HLA-A2− lines expressing or not expressing the CMVpp65 antigen (lower panels). GRE is HLA-A2+, COL is HLA-A2 negative.

8b) Progression of tumor growth of an HLA-A2+ MelA+ melanoma line implanted in humanized NOD-SCID b2 m$^{-/-}$ immunodeficient mice vaccinated with the pDC line GEN2.2 (GEN) pulsed with the MelA or FluM1 peptides and irradiated.

8c) Flow cytometry analysis of tumor suspensions showing the presence of MelA-specific CD8 T cells at the level of the tumor site of a vaccinated humanized mouse. The percentage indicated corresponds to the percentage of tetramer+ cells among the CD8+ T cells.

Figure 9:
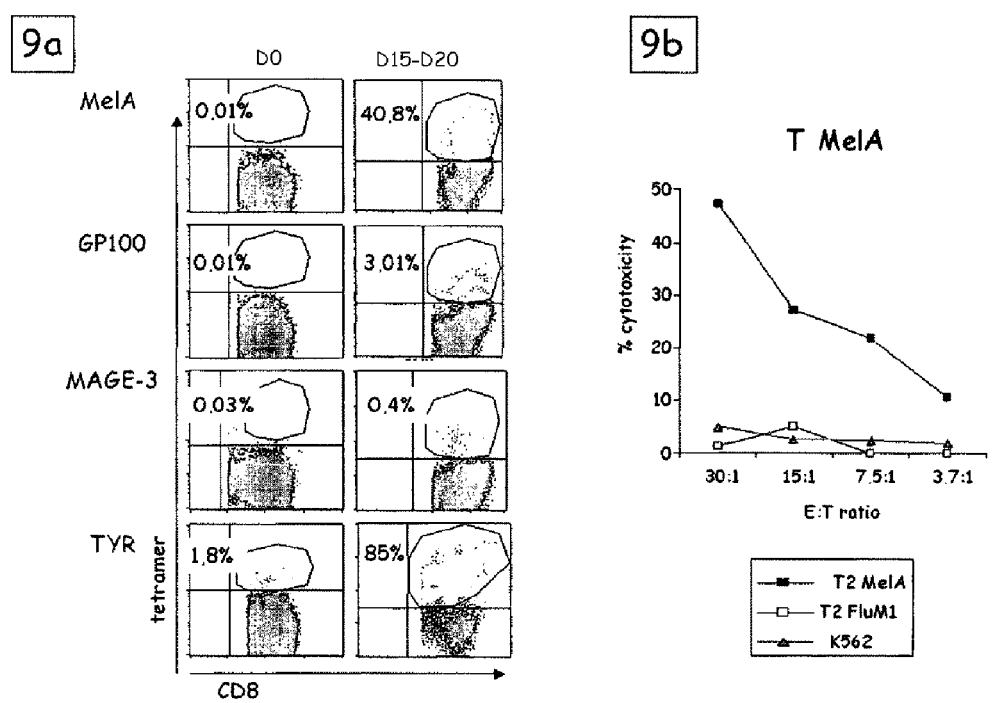

FIG. 9: The pulsed and irradiated pDC line according to the invention makes it possible to induce and amplify CD8 T cells which are specific and functional in patients suffering from melanoma 9a) Flow cytometry analysis of the CD8+ T cells on D0 and on D15-20 of the culture of PBMCs, derived from HLA-A2+ patients suffering from melanoma, with the pDC line pulsed with peptides derived from the MelA, GP100, MAGE3 and tyrosinase (TYR) antigens, and irradiated. The percentages indicated correspond to the percentages of tetramer+ cells among the CD8+ T cells.

9b) Cytotoxic activity of the MelA-specific CD8+ T cells generated by the pulsed pDC line according to the invention, using PBMCs derived from HLA-A2+ patients suffering from melanoma, with respect to the T2 cells pulsed with the MelA peptide or a control peptide.

Figure 10:
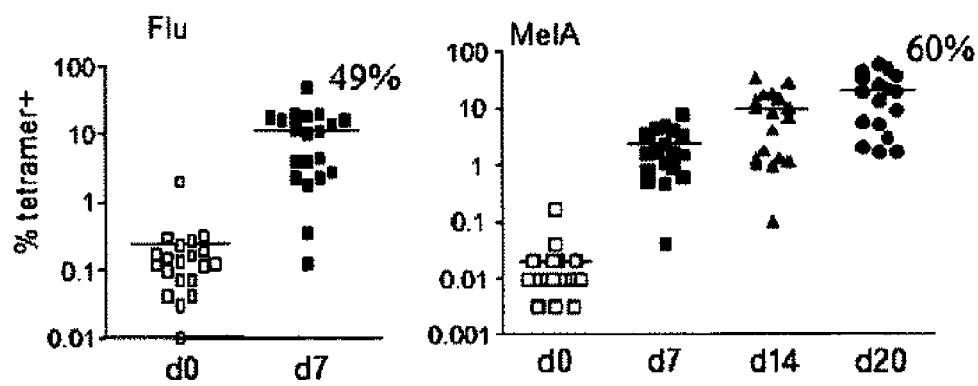

FIG. 10: Induction of specific primary and memory CD8 T responses in vitro

Percentages of specific CD8+ T cells on day (D) 0 and at various times of the culture of PBMCs, derived from healthy donors, with the pDC line GEN2.2 pulsed with a peptide (respectively, viral peptide Flu M1 and tumor peptide MelA), analyzed by flow cytometry using tetramers. The percentages indicated correspond to the percentages of tetramer+ cells among the CD8+ T cells. Each point represents the results obtained with one donor (n=20 for Flu and n=18 for MelA). The mean is represented by a horizontal bar, the percentages indicated are the maxima reached.

FIG. 11: Effect of the irradiation on the activation of the pDC line and on its ability to induce a specific T response 11a) Flow cytometry analysis of the level of expression of the HLA-A2 molecules and of the stimulatory molecules at the surface of the pDC line which has been irradiated or not irradiated, and then cultured for 24 h, in comparison with myeloid DCs treated under the same conditions.

11b) Flow cytometry analysis of the level of expression of the HLA-A2 and CD40 molecules at the surface of the pDC line, in the presence of ligands of TLR7 (inactivated influenza virus: Flu) or of TLR9 (CpGA), said line having been irradiated or not irradiated, and then cultured for 24 h.

11c) Comparative flow cytometry analysis of the percentage of specific CD8+ T cells after 7 days of culture of PBMCs, derived from healthy donors, with the pDC line GEN2.2 which has been irradiated or not irradiated, and pulsed with the Flu peptide. The percentages indicated correspond to the percentages of tetramer+ cells among the CD8+ T cells.

FIG. 12: Efficacy of the pDC line in terms of amplifying specific antitumor CD8+ T cells, ex vivo, using PBMCs and TILs from patients with a stage I-IV melanoma The PBMCs (n=12) and TILs (n=6) originating from patients with melanomas (stages I to IV) were cultured with the pDC line pulsed with a tumor peptide (a-b) or a mix of four tumor peptides (MelA, GP100, TYR and/or MAGE-3) (c-d), and irradiated. The cultures were restimulated each week, in the presence of IL2.

a-d) Flow cytometry analysis of the percentage of tetramer+ CD8+ T cells during cultures (20 days) of the PBMCs (a, b) or of the TILS (c, d) with the pulsed and irradiated pDC line. A representative experiment carried out with PBMCs (a) or TILs (c) is shown (analysis on D20). The results of all the experiments carried out are shown for the PBMCs (b) and for the TILs (d), with an initial measurement (D0) of the percentages of tetramer+ CD8+, and a measurement after 7, 14 and 20 days of culture. Each point represents one patient, the horizontal bars represent the mean, and the percentages indicated are the maxima reached.

e-h) Analysis of the functionality and of the specificity of the antitumor T lymphocytes induced by the pulsed and irradiated pDC line, using the PBMCs and TILs. e) Measurement of IFNγ secretion by the T lymphocytes generated from PBMCs by the pDC line pulsed with the MelA or GP100 peptides, by flow cytometry, after restimulation by T2 cells pulsed with the relevant peptide or a control peptide (representative experiment of 8 carried out with PBMCs (n=6) and TILs (n=2)). The percentages indicated correspond to the percentages of tetramer+ CD8+ T cells producing IFNγ.

f-h) Measurement of the cytotoxicity ($^{51}$Cr release) of the T lymphocytes generated. The T lymphocytes purified after 15 to 20 days of culture from PBMCs or TILs were used as effectors in a cytotoxicity test against the pulsed T2 line, allogenic and autologous melanoma cells, and also autologous CD45+ nontumor cells. f) The PBMCs (patient #9) were activated with the pDC line pulsed with the MelA peptide, and the TILs (patient #11) were activated with the pDC line pulsed with a mixture of the four peptides MelA, GP100, TYR and MAGE-3. These experiments are representative of 12 carried out with PBMCs and 6 carried out with TILs. g) Percentage lysis of the autologous tumor cells in comparison with the autologous CD45+ nontumor cells, initially and after stimulation of TILs. These two experiments are representative of six TIL samples analyzed. h) Comparison of the efficacy of lysis of the indicated targets by the TILs before and after stimulation with the pDC line pulsed with a mixture of four tumor peptides. The mean+/−standard error of the lysis percentages measured at the 60:1 ratio is shown (n=6).

EXAMPLES

Example 1

The pDC line GEN2.2 makes it possible to induce primary and memory CD8 T responses specific for an antigen of interest in vitro using cells from healthy individuals The ability of the GEN2.2 cells to induce an antigen-specific CD8 T response in a semi-allogenic context was tested by culturing cells of the GEN2.2 line (hereinafter: GEN2.2 cells), pulsed with a peptide of interest and irradiated, with peripheral blood mononuclear cells (PBMCs) from HLA-A2+ healthy volunteer donors.

Figure 1:
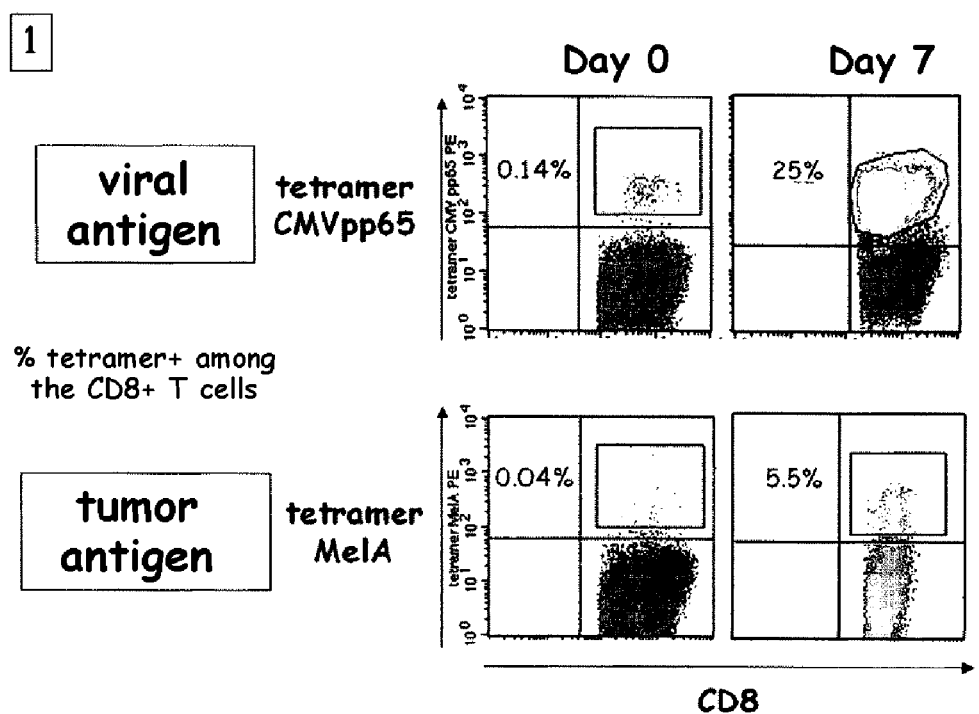
FIG. 1: Induction of specific primary and memory CD8 T responses in vitro

In order to pulse the GEN2.2 cells with a peptide of interest, said cells are washed 3 times in complete RPMI medium (RPMI 1640 Glutamax supplemented with 1 mM sodium pyruvate, 20 µg/ml gentamicin, 10 µM nonessential amino acids) without FCS, and resuspended at $1 \times 10^6$/ml. The cells are supplemented with 100 ng/ml of β2-microglobulin and incubated for 10 min at 37° C. (incubator). The peptide of interest is then added in a proportion of 10 µM. The cell suspension is then incubated for 3 h at 37° C. (incubator) with regular stirring. The cells are then washed, irradiated at 30 Gy and resuspended at $2 \times 10^5$/ml in complete RPMI medium supplemented with 10% of fetal calf serum. The PBMCs are purified by means of Ficoll using a bag of blood from a healthy donor. They are resuspended at $2 \times 10^6$/ml in complete RPMI medium supplemented with 10% of fetal calf serum. The pulsed and irradiated GEN2.2 cells are cocultured with the HLA-A2+ semi-allogenic PBMCs in a 24-well plate ($2 \times 10^5$ GEN2.2+$2 \times 10^6$ PBMCs/2 ml) for 7 days at 37° C. The phenotype of the CD8 T cells is determined at the beginning of the experiment (D0) and after 7 days of culture (D7). The specificity of the CD8 T cells is analyzed by labeling with tetramers (FIG. 1).

The coculturing of PBMCs with the pDC line GEN2.2 pulsed with a peptide derived from viral or tumor antigens and irradiated makes it possible to induce and to amplify CD8 T cells specific for the peptide of interest with high efficacy in only 7 days of culture. We demonstrated the induction of primary responses directed against the tumor antigens MelA, GP100, MAGE-3, tyrosinase and NY-ESO1, and of memory responses directed against the viral antigens FluM1, CMVpp65, EBV BMLF1 and EBV LMP2, using this strategy.

Example 2

The pulsed and irradiated pdc line enables massive amplification of CD8 t cells specific for an antigen of interest In order to optimize the induction of specific T cells, the cells were restimulated regularly with the pulsed and irradiated GEN2.2 cells, in the presence of IL2. For this, the cells are cultured as described above. After 7 days of culture, the cells are recovered, washed, counted and suspended at $2 \times 10^6$/ml in complete RPMI medium supplemented with 10% of fetal calf serum. They are put back in culture in 24-well plates, with pulsed and irradiated GEN2.2 cells in a proportion of $2 \times 10^5$/ml in the presence of IL2 at 200 U/ml. This process is repeated every 7 days. The percentage and the absolute number of CD8 T cells specific for the peptide used are evaluated before each restimulation.

As shown in FIG. 2, repeated stimulations with the pulsed irradiated GEN2.2 line, in the presence of cytokines (IL-2), enable massive amplification of CD8 T cells specific for the peptide used, with a very high efficacy. This can result in exclusive amplification of the CD8 T cells specific for the peptide of interest (more than 97% of tetramer+ CD8 T cells obtained) and in concomitant amplification thereof (multiplication by a factor of 20 000 000 of the absolute number of specific CD8 T cells) both for viral antigens and for tumor antigens.

Example 3

The pDC line GEN2.2 enables the simultaneous induction of multispecific primary or memory CD8 T responses In order to evaluate the possibility of inducing multi-specific T responses, the cells of the GEN2.2 line were pulsed simultaneously with several peptides derived from viral antigens (BMLF1, LMP2) or from tumor antigens (MelanA, GP100, tyrosinase, MAGE-3), and then irradiated. They were then cultured with HLA-A2+ semi-allogenic PBMCs, according to the protocols described above. Within these PBMCs, the initial percentages of tetramer+ cells (BMLF1, LMP2, MelA, GP100, TYR or MAGE-3) among the CD8+ T lymphocytes were strictly less than 0.05%. The amplification of CD8 T cells specific for each of the peptides used is analyzed by tetramer labeling at 7 days (for EBV, the BMLF and LMP2 peptides, FIG. 3a) or at 21 days of culture with two restimulations (for MelA, GP100, TYR and MAGE-3, FIG. 3b).

The use of the pDC line pulsed with a mixture of various peptides therefore makes it possible to simultaneously induce CD8 T cells specific for each of the peptides used, both in viral models and in tumor models.

Example 4

The specific T cells generated by the pDC line GEN2.2 exhibit very good functionality in vitro Three methods were used to evaluate the functionality of the CD8 T cells generated by the pulsed pDC line GEN2.2: cytotoxicity test, IFNγ secretion and membrane expression of CD107 after specific restimulation.

The cytotoxic activity of the specific T cells generated by the GEN2.2 line is evaluated by means of a $^{51}$Cr release test. For this, after stimulation of semi-allogenic PBMCs with GEN2.2 cells which have been pulsed with the MelA peptide and irradiated, the cells are recovered and the CD8+ T lymphocytes are purified (EasySep CD8 T sorting by negative selection) and placed together with $^{51}$Cr-labeled target cells at various ratios (E:T ratio range of from 60:1 to 7.5:1) for 4 h. The $^{51}$Cr in the supernatant is then assayed. The anti-MelA T cells are, for example, capable of efficiently lysing HLA-A2+ tumor cells which express Melan-A (Me275) but have no cytotoxic activity on tumor cells which do not express MelA (A375) or which are not HLA-A2 (COL0829) (FIG. 4a).

The effector capacity of the specific T cells was also evaluated by virtue of their ability to secrete IFNγ and to express surface CD107 after specific restimulation. For this, after stimulation of semi-allogenic PBMCs with GEN2.2 cells which have been pulsed with the fluM1 peptide and irradiated, the cells are recovered and counted and tetramer labeling is carried out (30 min at ambient temperature). After washing, the cells are suspended at $1 \times 10^6$/200 µl in RPMI medium containing 10% FCS. The T2 cells which have been pulsed with the peptide of interest (fluM1) or a control peptide (LMP2) are optionally added (effector cell:restimulating cell ratio=10:1). For IFNγ secretion, the cells are restimulated for 5 h 30 at 37° C. in the presence of brefeldin A (GolgiPlug at 1 μl/ml) for the final 3 hours. After labeling of surface antigens (CD3, CD8), intracellular labeling of IFNγ is then carried out (FIG. 4b). In order to measure the CD107 expression, anti-CD107a and anti-CD107b antibodies (20 ml/$10^6$ cells) are added for the entire duration of the restimulation, and the cells are incubated for 5 h at 37° C. in the presence of monensin (GolgiSTOP at 0.67 μl/ml) for the last 4 hours. Labeling of surface antigens (CD3, CD8) is then carried out (FIG. 4b). The IFNγ and CD107 labeling is analyzed on the tetramer+ CD8+ T cells. Thus, anti-FluM1 CD8+ T cells generated by virtue of the GEN line are capable of secreting IFNγ and of expressing CD107 specifically after restimulation with FluM1-pulsed T cells and not after restimulation with T2 cells pulsed with another peptide (T2 LMP2) or in the absence of restimulation (FIG. 4b).

The antigen-specific CD8 T cells generated by the pDC line GEN2.2 are therefore capable of killing target cells which express this antigen in an HLA-restricted manner. They specifically secrete IFNγ and express CD107 after restimulation with cells presenting the peptide for which they are specific, in the correct HLA context.

Example 5

The pDC line GEN2.2 makes it possible to Induce and Amplify CD8 T cells specific for an antigen of interest with greater efficacy than myeloid dendritic cells (mDCs) and confers a greater functional capacity on said T cells We compared the capacities of the pDC line GEN2.2 for inducing specific CD8 T cells with those of allogenic or autologous myeloid dendritic cells (mDCs), and evaluated their functional properties.

In order to generate the mDCs, monocytes were purified by negative sorting (use of the EasySep® kit, according to the manufacturer's recommendations) from PBMCs and cultured at $0.5 \times 10^6$ cells/ml in RPMI medium containing 10% FCS in the presence of GM-CSF (500 U/ml) and of IL4 (10 ng/ml) for 6 days. The mDCs and the GEN2.2 cells were then pulsed with a peptide of interest as described in Example 1, irradiated, and cultured with HLA-A2+ PBMCs which were semi-allogenic or autologous (for the mDCs). Restimulations were carried out every 7 days in the presence of IL2 (200 U/ml) or of IL15 (5 ng/ml). The percentage (FIG. 5a) and the absolute number (FIG. 5b) of tetramer+ CD8 T cells is evaluated, respectively, at 7 and 20 days of culture after stimulation of the PBMCs with GEN2.2 cells, allogenic mDCs or autologous mDCs pulsed with MelA. The GEN2.2 line allows a much more efficacious induction of anti-MelA T cells in comparison with the allogenic or autologous mDCs under basal conditions or in the presence of cytokines. The affinity of the CD8 T cells generated under the various conditions is measured by the dissociation of the tetramer at 37° C. For this, tetramer labeling of the specific CD8 T cells is carried out (30 min at 4° C.). After washing, the cells are incubated at 37° C. After various incubation times (from 0 to 16 h), the cells are recovered and fixed for flow cytometry analysis. The dissociation of the tetramer is evaluated as percentage of the initial tetramer labeling (FIG. 5c). The avidity of the CD8 T cells generated under the various conditions is measured by virtue of their cytotoxic activity on T2 cells pulsed with decreasing peptide concentrations (from 1 to 0.0001 μM). The cytotoxicity is expressed as percentage of the maximum cytotoxicity observed (FIG. 5d). The anti-MelA T cells generated by the GEN2.2 line exhibit higher affinity and higher avidity compared with the anti-MelA T cells generated by the allogenic or autologous mDCs.

The pDC line GEN2.2 is much more efficacious than the mDCs for inducing specific T cells (higher percentage of tetramer+ cells obtained under the same conditions) and especially for amplifying the specific T cells (ten times greater amplification with the pDCs compared with the mDCs). In addition, the GEN2.2 line confers a greater functional capacity on the specific T cells since they acquire greater affinity and greater avidity than the cells generated with the mDCs.

Example 6

The specific T cells generated by the pDC line exhibit very good antitumor activity in vivo by adoptive transfer The functional efficacy of the specific T cells generated in vitro by the pDC line GEN2.2 was evaluated in vivo by virtue of their ability to inhibit the development of a human tumor implanted in an immuno-deficient mouse.

A tumor is established in NOD-SCID b2 $m^{-/-}$ mice by injection of 1 to $2.5 \times 10^6$ tumor cells subcutaneously into the flank. In parallel, CD8 T cells specific for an antigen of interest are generated in vitro with the GEN2.2 line as described above. After selection of the CD8+ T cells by negative sorting (using the EasySep® kit according to the manufacturer's recommendations), 1 to $5 \times 10^6$ CD8+ T cells are then transferred intra-tumorally by means of 4 injections 4-5 days apart. The progression of tumor growth is then measured. FIG. 6a shows the progression of growth of the GRE pp 65 tumor (HLA-A2+ CMVpp65+) after adoptive transfer of anti-CMVpp65 or anti-FluM1 CD8+ T cells. FIG. 6b shows the comparison of the tumor sizes 20 days after implantation thereof, after treatment with anti-CMVpp65 or anti-FluM1 CD8+ T cells (each point represents one mouse).

The anti-CMVpp65 T cells generated in vitro by the GEN line therefore make it possible to inhibit the development of an HLA-A2+ CMVpp65+ tumor. The observed therapeutic efficacy of the injected cells is HLA-restricted and antigen-restricted since this treatment does not make it possible to inhibit the development of tumors which are not HLA-A2 (COL pp 65) or which do not express the antigen against which they are directed (GRE IE) (FIG. 6c).

Example 7

The pDC line makes it possible to induce a specific primary or memory T response in vivo by vaccination In order to evaluate the ability of the pDC line GEN2.2 to induce a specific T response in vivo, a model of humanized mice was developed (immunodeficient mice reconstituted with a human immune system).

For this, $50 \times 10^6$ PBMCs are injected intraperitoneally into NOD-SCID b2m–/–mice. The following day, $5 \times 10^6$ GEN2.2 cells which have been pulsed with a peptide of interest and irradiated are injected intraperitoneally. The vaccination is optionally repeated once a week. At various times after vaccination (9 days for CMV vaccine, 30 days for MelA vaccine), the induction of specific CD8+ T cells is evaluated at the site of immunization (lavage), in the circulation and in the secondary lymphoid organs (spleen, lymph nodes). For this, a blood sample is taken from the mice, which are then sacrificed. A peritoneal lavage with 15 ml of RPMI medium makes it possible to recover the cells from the site of immunization. The lymphoid organs are then removed and a cell suspension is prepared after digestion with 2.5 mg/ml collagenase. Tetramer-labeling of the specific CD8 T cells is carried out. FIG. 7a shows an example obtained with one mouse in each case, FIG. 7b shows the initial level of tetramer+ CD8 T cells among the PBMCs and all the responses to the CMV or MelA vaccination obtained. Thus, a vaccination with pulsed pDC line according to the invention makes it possible to very efficaciously induce specific CD8 T responses in vivo, both at the site of immunization and also in the circulation and in the secondary lymphoid organs. We demonstrated a response to vaccination in vivo with the viral antigens FluM1, EBV BMLF1, EBV LMP2 and CMVpp65, and with the tumor antigens MelA, GP100, MAGE-3 and tyrosinase.

Injection of the product (pulsed, irradiated pDC line GEN2.2) in vivo makes it possible to induce specific T responses directly in the recipient, both for viral antigens and for tumor antigens. The response levels obtained are high compared with the known reference levels. This demonstrates the feasibility of using the product as a cell vaccine. This efficacy provides proof for the preclinical concept of the therapeutic efficacy of this product as a cell vaccine.

Example 8

The specific T cells generated in vivo after vaccination with the pDC line exhibit very good functionality We evaluated the therapeutic efficacy of the response induced in vivo after vaccination, firstly, through the ex-vivo cytotoxic activity of the specific CD8 T cells and, secondly, through the effect on the development of a tumor in vivo.

NOD-SCID b2 $m^{-/-}$ mice were reconstituted with $50 \times 10^6$ PBMCs injected intraperitoneally, and were then vaccinated with $5 \times 10^6$ GEN2.2 cells which had been pulsed with a CMV-derived peptide (CMVpp65) and irradiated. Nine days after vaccination, the CD8+ T cells were purified from samples taken from the immunization site and from the lymphoid organs (negative sorting with the EasySep kit, used according to the manufacturer's recommendations) and their cytotoxic activity was evaluated against T2 cells pulsed with the CMVpp65 peptide or a control peptide (fluM1) (FIG. 8a), and on HLA-A2+ tumor cells (GRE pp65) or HLA-A2− tumor cells (COL pp 65), expressing the corresponding antigen or not expressing the corresponding antigen (GRE IE) (FIG. 8a). As shown in FIG. 8a, the specific CD8 T cells generated in vivo after vaccination exhibit cytotoxic activity on T2 cells and on HLA-A2+ tumor cells expressing the antigen for which they are specific.

In order to evaluate the therapeutic efficacy of the vaccination with the pulsed pDC line according to the invention on the development of a tumor, NOD-SCID b2 $m^{-/-}$ mice were reconstituted with $50 \times 10^6$ PBMC cells injected intraperitoneally, and were then vaccinated with $5 \times 10^6$ cells of the GEN2.2 line pulsed with a peptide derived from MelA or from Flu (FluM1), once a week. Five to ten days after the first vaccination, $10 \times 10^6$ HLA-A2+ MelA+ tumor cells (Me275) were implanted in the flank subcutaneously. The progression of the tumor growth was then observed (FIG. 8b). The presence of MelA-specific CD8 T cells was then investigated at the tumor site by flow cytometry analysis of a suspension of the tumor 1 month after its implantation (FIG. 8c). Thus, the vaccination with the pulsed pDC line according to the invention makes it possible to inhibit the development of an HLA-A2+ tumor which expresses the antigen of interest used to pulse the GEN cells. The CD8 T cells specific for the peptide of interest, generated by the vaccination, are capable of migrating to the site of expression of the antigen and of lysing the tumor cells.

The examples demonstrate that the specific CD8 T cells induced in vivo by vaccination exhibit HLA-restricted and antigen-restricted cytotoxic efficacy ex vivo, and are capable of migrating to the site of expression of the antigen for which they are specific and of inhibiting the development of a tumor.

Example 9

The pDC line GEN2.2 makes it possible to induce and amplify CD8 T cells which are specific for antigens of interest and functional, using cells from patients suffering from cancer In order to analyze whether the pulsed pDC line according to the invention makes it possible to amplify a specific T response in patients suffering from cancer, we cultured PBMCs derived from HLA-A2 patients suffering from stage 1V melanoma with the GEN2.2 cells pulsed with the peptides derived from MelA, GP100, MAGE-3 or tyrosinase according to the same protocol as in Example 2. The specific CD8+ T cells are analyzed by flow cytometry before stimulation and after 3 stimulations with the pulsed GEN cells (FIG. 9a). The functionality of the CD8 T cells generated was then evaluated by measuring their cytotoxic activity on T2 cells pulsed with the peptide of interest or a control peptide (FluM1) (FIG. 9b) according to the same protocol as in Example 4.

The pDC line GEN2.2 therefore makes it possible to induce a massive amplification of CD8 T cells specific for various tumor antigens using the cells from patients suffering from cancer. The cytotoxic activity of the T cells generated confirms their antitumor functionality.

Example 10

The pDC line GEN2.2 makes it possible to induce primary and memory CD8 T responses specific for an antigen of interest in all the donors tested The ability of the GEN2.2 cells to induce an antigen-specific CD8+ T response in a semi-allogenic context was tested by culturing the pulsed and irradiated cells of the pDC line in the presence of PBMCs from HLA-A*0201+ healthy volunteer donors. The induction of a memory response is evaluated using the MelanA peptide; the induction of a memory response is evaluated using the flu M1 peptide of the influenza template.

In order to pulse the GEN2.2 cells with a peptide of interest, said cells are washed 3 times in complete RPMI medium (RPMI 1640 Glutamax supplemented with 1 mM sodium pyruvate, 20 µg/ml gentamicin, 100 µM nonessential amino acids) without FCS, and resuspended at $1 \times 10^6$/ml. The cells are supplemented with 100 ng/ml of β2-microglobulin and incubated for 10 min at 37° C. (incubator). The peptide of interest is then added in a proportion of 10 µM (Flu M1) or 1 µM (MelA). The cell suspension is then incubated for 3 h at 37° C. (incubator) with regular stirring. The cells are then washed, irradiated at 30 Gy and resuspended at $2 \times 10^5$/ml in complete RPMI medium supplemented with 10% of fetal calf serum. The PBMCs are purified, using Ficoll, from bags of blood from healthy donors. They are resuspended at 2×10⁶/ml in complete RPMI medium supplemented with 10% of fetal calf serum. The pulsed and irradiated GEN2.2 cells are cocultured with the HLA-A2+ semi-allogenic PBMCs in a 24-well plate (2×10$^5$ GEN2.2+2×10$^6$ PBMC/2 ml) for 7 to 20 days at 37° C. Weekly restimulations of the cultures in the Mel A model are carried out, under the same conditions as initially, with addition of IL-2 (200 U/ml). The phenotype of the CD8 T cells is evaluated at the beginning of the experiment (D0) and after 7 days of culture (D7) for the measurement of the anti-FluM1 response, and after 7, 14 and 20 days for the measurement of the anti-MelA response. The specificity of the CD8 T cells is analyzed by means of tetramer labeling (FIG. 10).

After 7 days of culture, the percentages of tetramer+ T lymphocytes specific for the Flu viral antigen are, on average, 11% (0.1% to 49%) (20 cultures prepared from the PBMCs of different donors). The percentages of antitumor T lymphocytes directed against MelA reach, on average, 22% (2% to 60%) after 20 days of culture (18 cultures prepared from the PBMCs of different donors). The respective initial percentages of anti-Flu and anti-MelA tetramer+ T lymphocytes were, on average, 0.23% and 0.02%.

In this example, we demonstrate that, with this strategy, it is possible, with 100% of the donors (HLA-A*0201) to amplify antigen-specific T lymphocytes in the context of a primary or memory response.

Example 11

Irradiation of the line of pDCs induces their maturation

The pulsed and irradiated cells of the pDC line induce the amplification of HLA-A*0201 specific T lymphocytes. We evaluated the effect of irradiation on the maturation of the pDCs, in comparison with myeloid dendritic cells.

Myeloid dendritic cells (MoDCs) were prepared from monocytes purified by negative sorting (using the EasySep® kit, according to the manufacturer's recommendations) from PBMCs, and cultured at 0.5×10⁶ cells/ml in RPMI medium containing 10% FCS in the presence of GM-CSF (500 U/ml) and of IL4 (10 ng/ml) for 6 days.

Figure 11A:
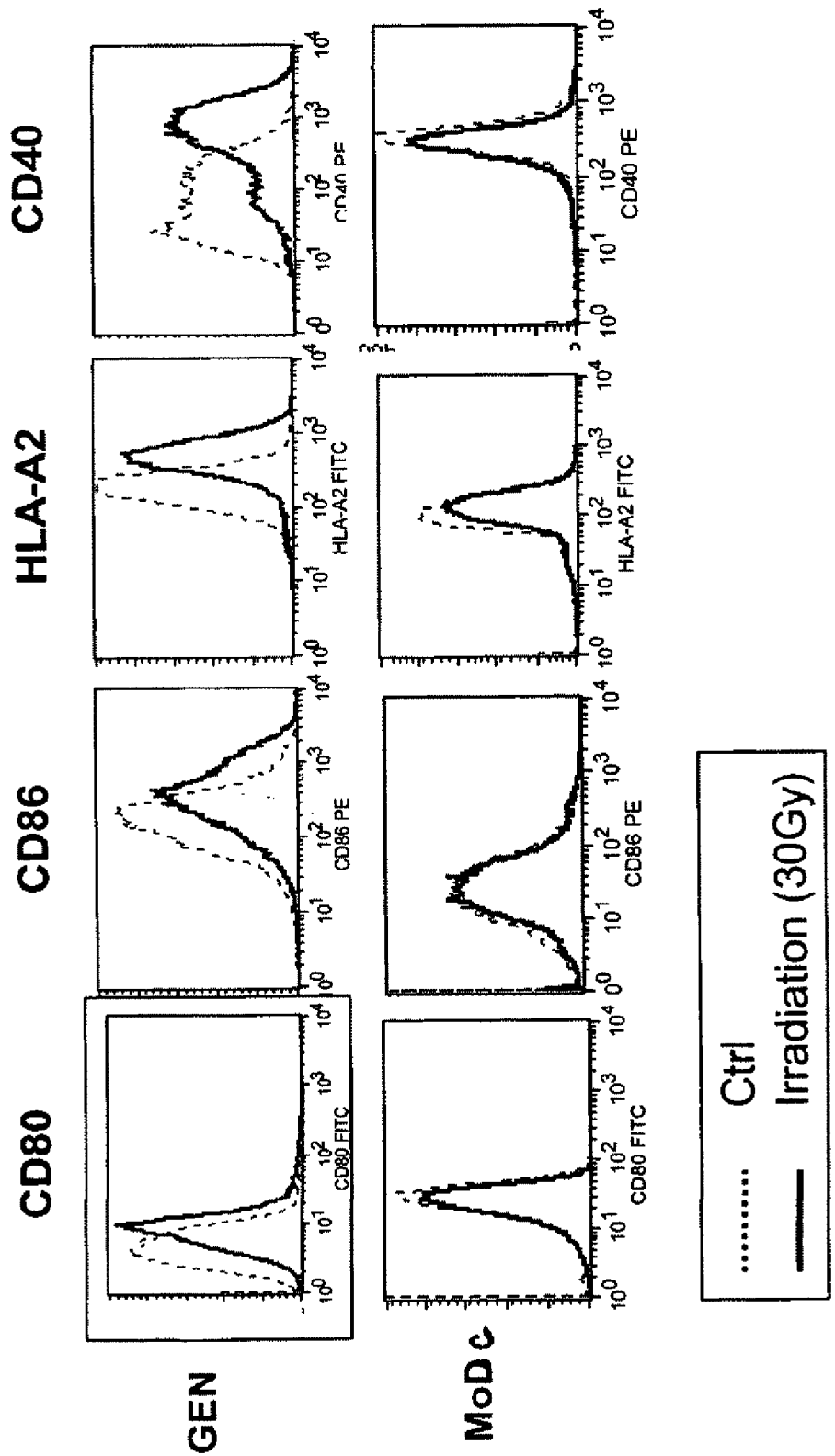

The cells of the GEN2.2 line and the myeloid dendritic cells (two different donors) were irradiated (30 Gray) and cultured in RPMI medium containing 10% FCS for 24 h, and then phenotyped. The expression levels of the CD40, CD80, CD86 and HLA-A2 molecules were monitored by flow cytometry (FIG. 11a). The irradiation induces an increase in the expression of these four molecules specifically in the pDCs and not in the MoDCs.

The effect of irradiation of the pDCs was compared with the effect of strong pDC maturation inducers, namely the influenza virus (Flu, ligand of TLR7) and CpG 2336 (ligand of TLR9). The cells of the GEN2.2 line were irradiated (30 Gray) or not irradiated, and were cultured in the presence or absence of inactivated influenza virus or CpG 2336, for 24 h. The cells were then phenotyped, and the HLA-A2 expression and CD40 expression were measured by flow cytometry. The irradiation induces maturation of the cells of the GEN2.2 line which is as great as that observed in the presence of the ligands of TLR7 or TLR9 (FIG. 11b).

In order to evaluate the influence of the maturation induced by irradiation of the GEN2.2 cells, on T response induction, the cells of the GEN2.2 line were pulsed with the Flu peptide, and then optionally irradiated. They were then cultured with HLA-A2+ semi-allogenic PBMCs, according to the protocols described above. The amplification of CD8 T cells specific for the Flu peptide is analyzed by means of tetramer labeling at 7 days (FIG. 11c). The nonirradiated pDCs are incapable of inducing the proliferation of specific T lymphocytes. The irradiation is therefore an essential element of the method described.

Example 12

The pulsed and irradiated pDC line enables massive amplification of tumor antigen-specific CD8 T cells from pbmcs and tils from patients with a melanoma The ability of the GEN2.2 cells to induce a tumor antigen-specific CD8 T response from the T lymphocytes from patients with a melanoma in a semi-allogenic context was tested by culturing cells of the GEN2.2 line (hereinafter: GEN2.2 cells), which had been pulsed with a peptide of interest, or a mixture of four peptides of interest, and irradiated, with peripheral blood mononuclear cells (PBMCs) or tumor-infiltrating T lymphocytes (TILs) from HLA-A2+ patients with a melanoma.

The PBMCs are purified, using Ficoll, from a tube of blood from individuals with a melanoma (n=12). The percentages of tetramer+ CD8+ T cells specific for the MelanA, GP100, tyrosinase and MAGE3 antigens were measured initially; they were, on average, between 0.02% and 0.03%.

The tumor cells and the TILs were purified from tumor biopsies dilacerated mechanically and then digested enzymatically (collagenase+DNAse). The tumor cells contained in these cell suspensions were separated from the TILs by virtue of their property of adhering to plastic. These tumor cells were cultured in RPMI containing 10% FCS, and amplified, before being frozen as used as a source of autologous tumor cells in certain experiments. The percentages of tetramer+ CD8+ T cells specific for the MelanA, GP100, tyrosinase and MAGE3 antigens were measured initially in the TILs; they were, on average, 0.17%, 0.2%, 0.05% and 0.3%, respectively.

The ability of the cells of the GEN2.2 line to amplify the tumor antigen-specific T lymphocytes from the PBMCs and TILs of patients was evaluated.

The GEN2.2 cells were pulsed, as described above, with a peptide of interest (concentration of each peptide: 10 μM), or a mixture of the four tumor antigen-derived peptides studied (concentration of each peptide: 2.5 μM). Briefly, the cell suspension is incubated for 3 h at 37° C. with the peptide(s), and then the cells are washed, irradiated at 30 Gy and resuspended at 2×10⁵/ml in complete RPMI medium supplemented with 10% of fetal calf serum.

Figure 12A:
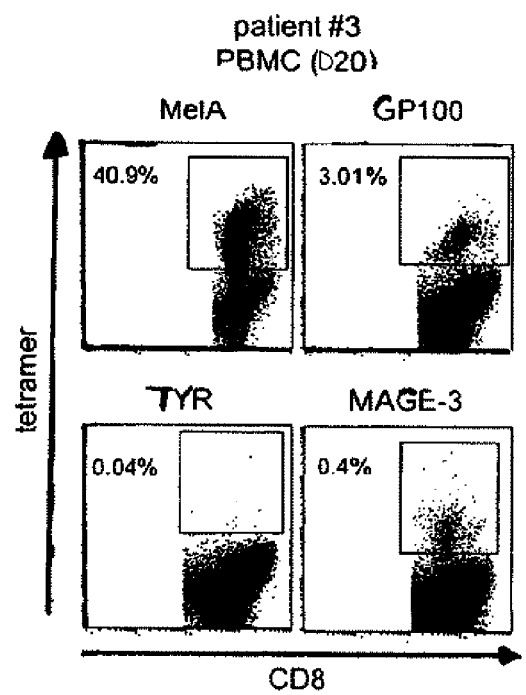
Figure 12B:
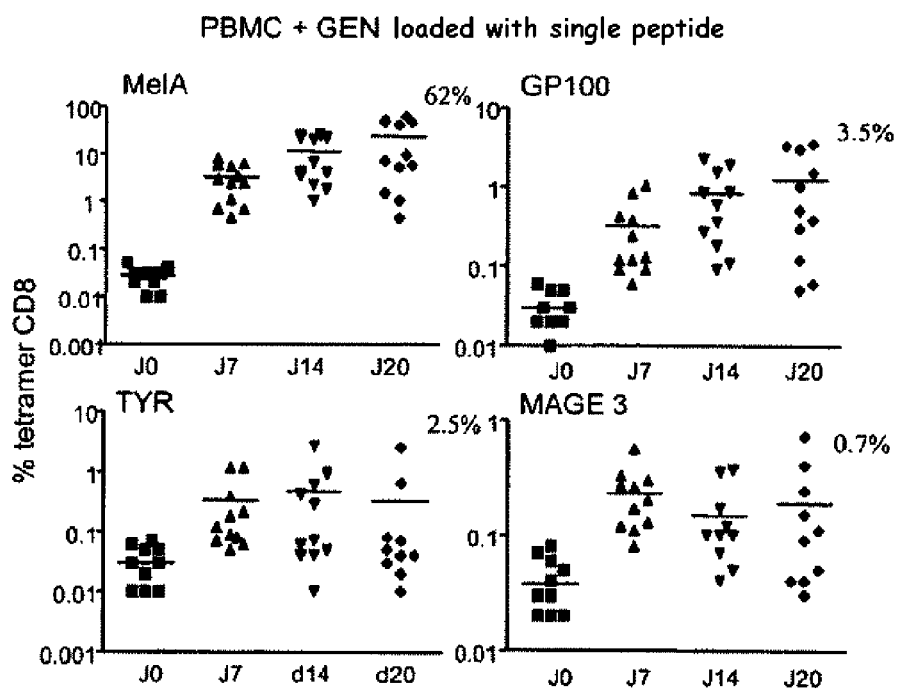
Figure 12C:
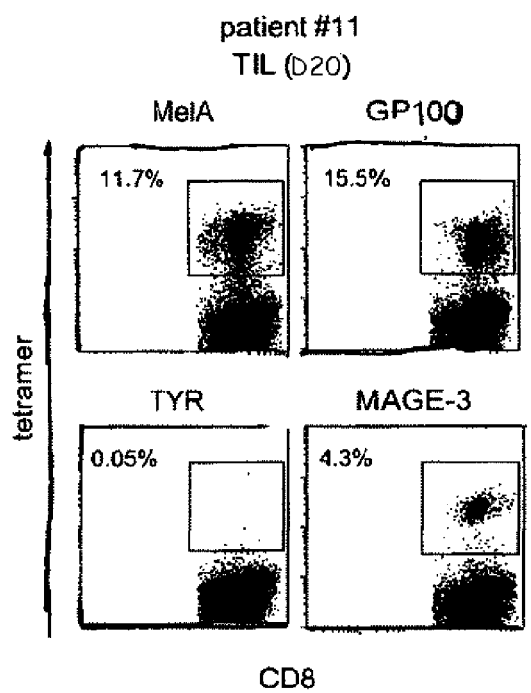
Figure 12D:
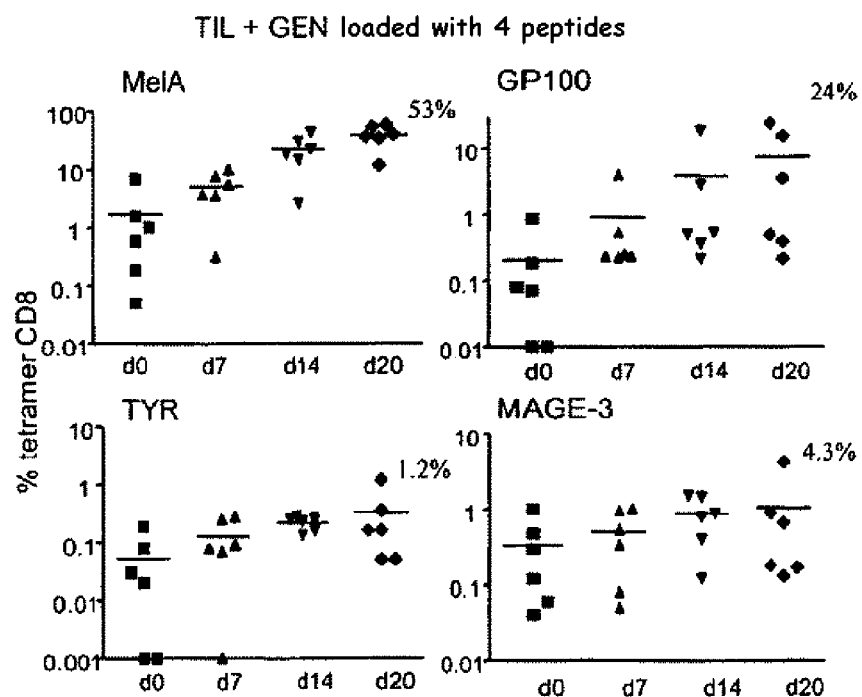

The PBMCs or the TILs are resuspended at 2×10⁶/ml in complete RPMI medium supplemented with 10% of fetal calf serum. The pulsed and irradiated GEN2.2 cells are cocultured with these HLA-A2+ semi-allogenic lymphocytes in a 24-well plate (2×10⁵ GEN2.2+2×10⁶ PBMC or TIL/2 ml) for 7 days at 37° C. The cultures are restimulated under the same conditions every 7 days, with the addition of IL2 (200 U/ml). The phenotype of the CD8 T cells is evaluated after 7, 14 and 20 days of culture (D7, D14, D21). The specificity of the CD8 T cells is analyzed by means of tetramer labeling, using the PBMCs (FIG. 12a and b) and using the TILs (FIG. 12c and d).

The coculturing of PBMCs with the pDC line GEN2.2, which has been pulsed with a tumor antigen-derived peptide and irradiated, makes it possible to induce and amplify CD8 T cells specific for the peptide of interest with great efficacy in only 7 days of culture. We demonstrated that the induction of such responses directed against the MelA, GP100, MAGE-3 or tyrosinase tumor antigens was possible using this strategy, starting from samples from patients with a melanoma, irrespective of the stage of their disease. The PBMCs from the patients respond against at least two of the antigens out of the four studied, and the TILs against at least three of these antigens.

Two methods were used to evaluate the functionality of the CD8 T cells generated by the pulsed pDC line GEN2.2: cytotoxicity test and IFNγ secretion after specific restimulation.

Figure 12E:
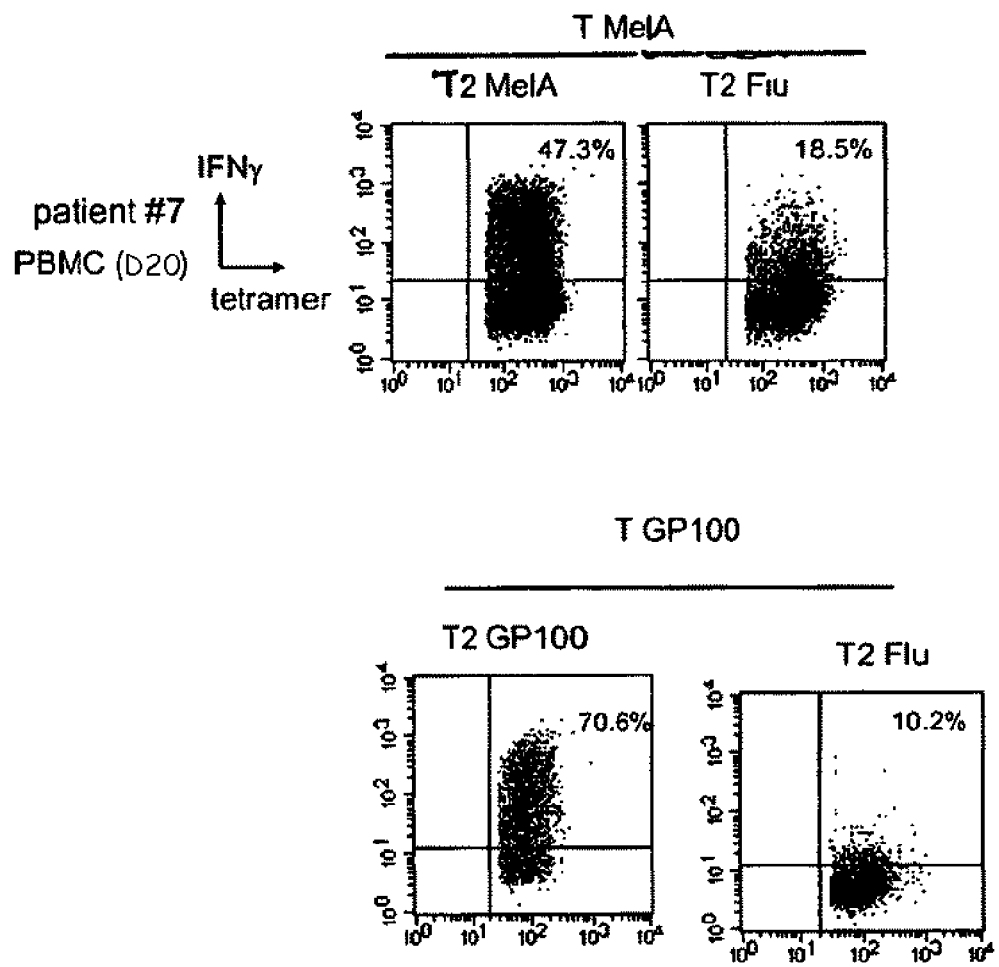

In order to evaluate the IFNγ secretion after restimulation, the cells amplified after culture are recovered and counted and tetramer labeling is carried out (30 min at ambient temperature). After washing, the cells are suspended at $1\times10^6/200$ μl in RPMI medium containing 10% FCS. The T2 cells pulsed with the peptide of interest (MelA or GP100) or a control peptide (Flu) are added (effector cell:restimulating cell ratio=10:1). The cells are restimulated for 5 h 30 at 37° C. in the presence of brefeldin A (GolgiPlug at 1 μl/ml) for the final 3 hours. After labeling of the surface antigens (CD3, CD8), intra-cellular labeling of IFNγ is then carried out (FIG. 12e). The analysis of the IFNγ labeling is carried out on the tetramer+ CD8+ T cells. Thus, anti-MelA CD8+ T cells generated by means of the GEN line are capable of secreting IFNγ specifically after restimulation with T2 cells pulsed with MelA, and not after restimulation with T2 cells pulsed with another peptide (T2 Flu), while GP100-specific T cells will secrete IFNγ in the face of T2 cells pulsed with GP100, but not with Flu (FIG. 12b).

Figure 12F:
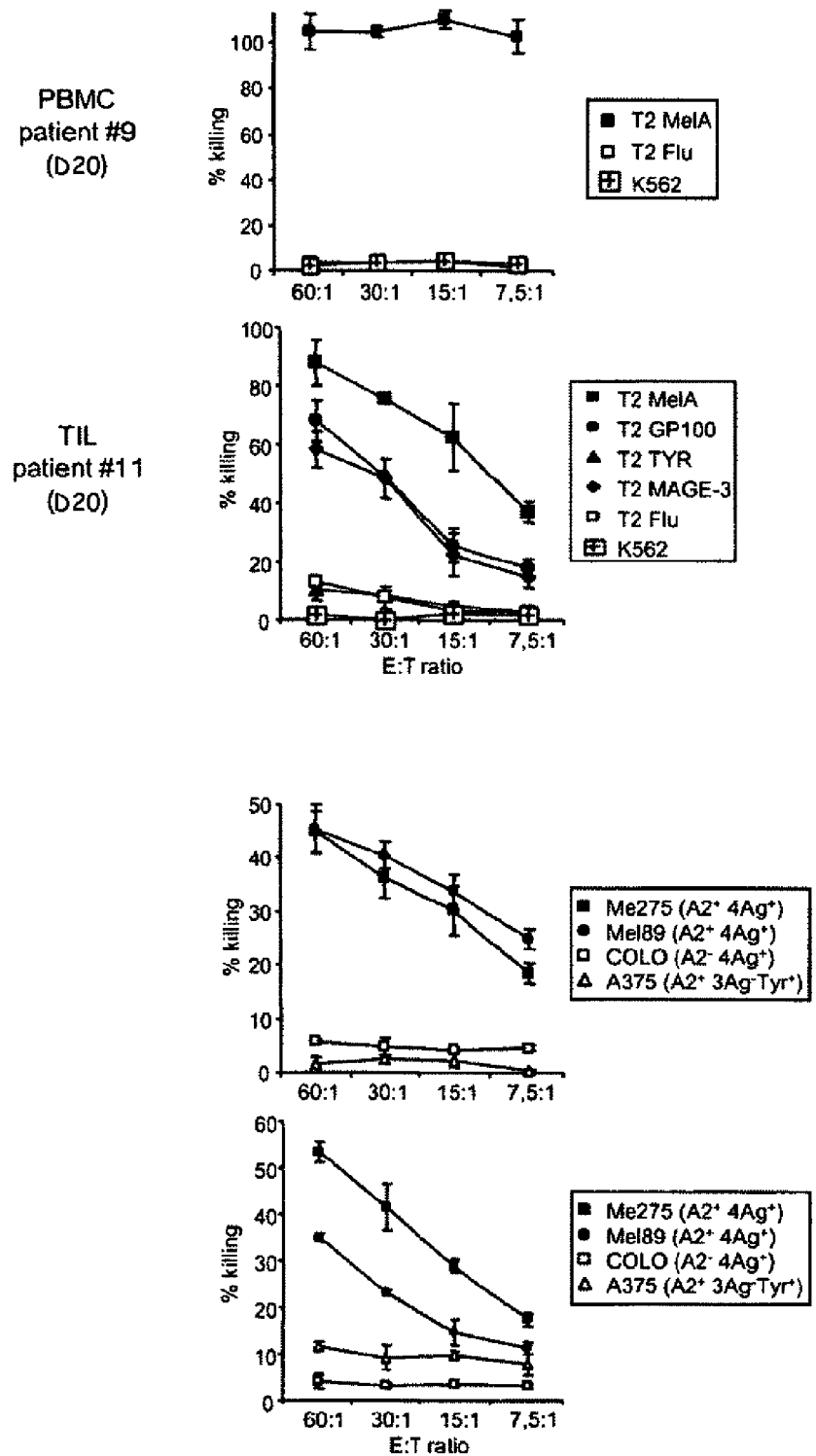

The cytotoxic activity of the specific T cells generated by the GEN2.2 line is evaluated by means of a $^{51}$Cr release test. For this, after stimulation of semi-allogenic PBMCs from patients with a melanoma, with GEN2.2 cells which have been pulsed with the MelA peptide and irradiated, the cells are recovered and the CD8+ T lymphocytes are purified (EasySep CD8 T sorting by negative selection) and placed together with $^{51}$Cr-labeled target cells at various ratios (E:T ratio ranging from 60:1 to 7.5:1) for 4 h. The $^{51}$Cr in the supernatant is then assayed. The anti-MelA T cells are, for example, capable of efficiently lysing HLA-A2+ tumor cells which express Melan-A (Me275 and Me189) but have no cytotoxic activity against tumor cells which do not express MelA (A375) or which are not HLA-A2 (COLO829) (FIG. 12f). Similar experiments were carried out with CD8+ T cells derived from TIL cultures stimulated with the GEN2.2 line pulsed with a mixture of the four tumor peptides studied. The example in FIG. 12f (TIL patient #11) shows that the lymphocytes generated which contain tetramer+ cells specific for MelA, GP100 and MAGE3 (FIG. 12c) lyse the target cells which express at least one of these antigens in the HLA-A2 context.

Figure 12G:
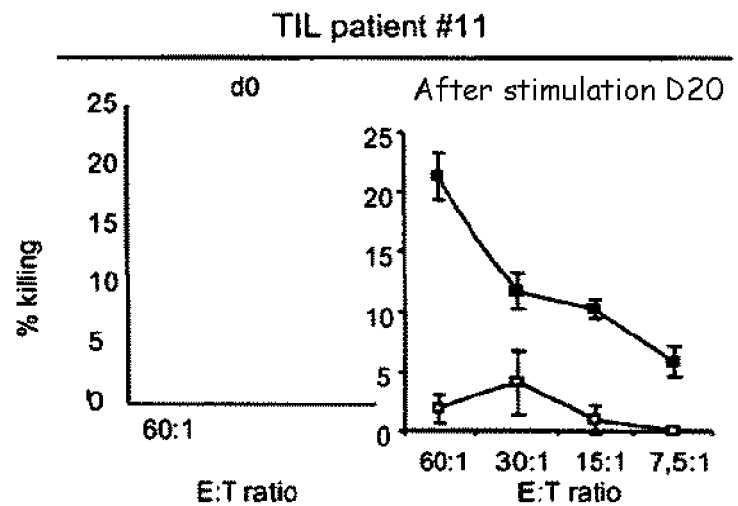
Figure 12G:
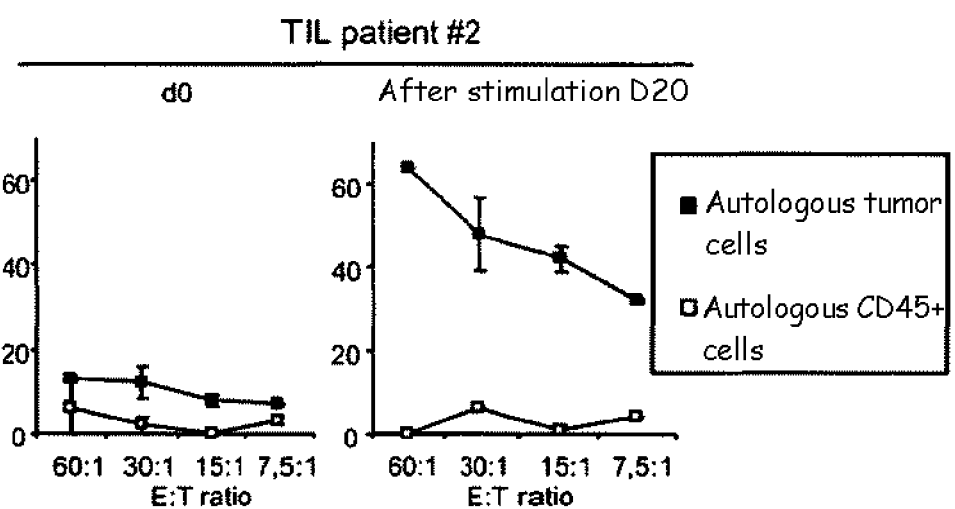
Figure 12H:
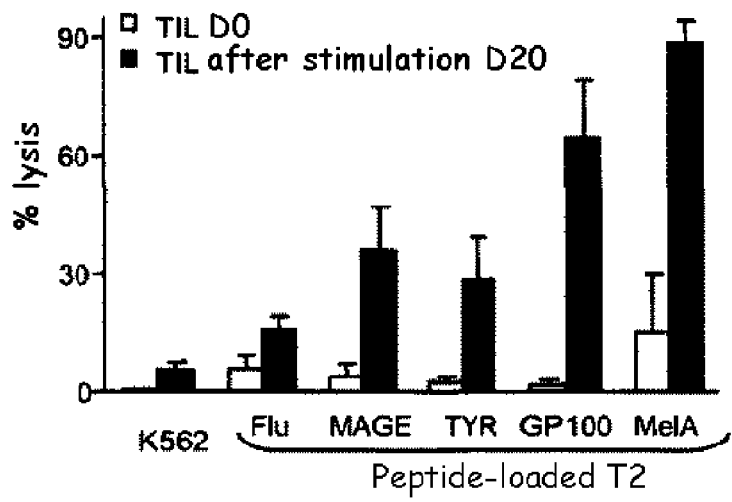
Figure 12H:
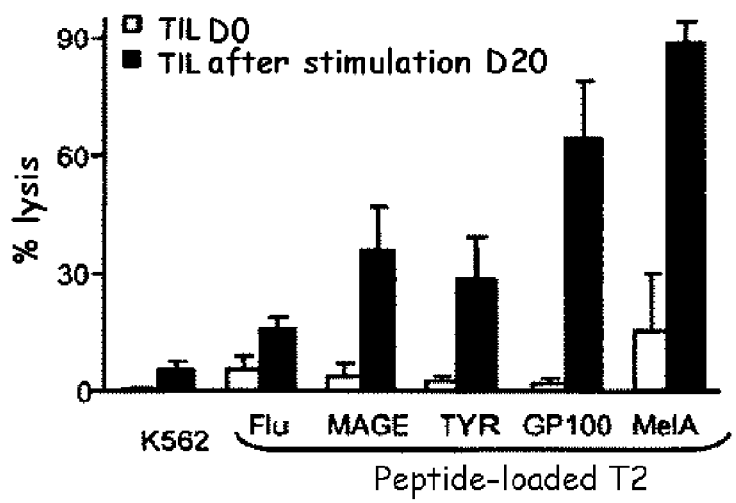
Figure 12H:
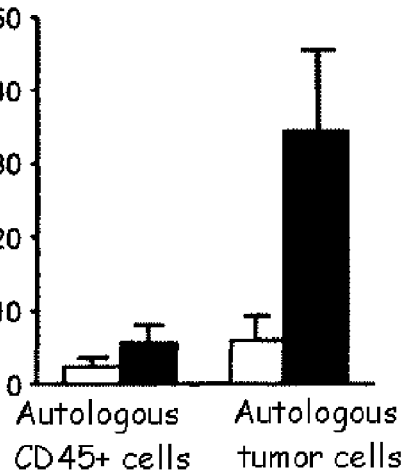

The cytotoxicity of the specific T cells generated by the GEN2.2 line pulsed with a mixture of the four tumor peptides studied was also measured against the autologous tumor cells of the patient, and autologous nontumor cells (purified CD45+ leucocytes). The two examples presented in FIG. 12g show, for two patients, that the TILs that were not initially cytotoxic against the autologous tumor cells acquire the ability to destroy the autologous tumor cells after stimulation with the GEN cells pulsed with the mixture of the four peptides. The autologous nontumor cells, for their part, are not lysed. These results were reproduced using samples from five patients (FIG. 12h).

The tumor antigen-specific CD8 T cells generated by the pDC line GEN2.2 from PBMCs and TILs from patients are therefore capable of killing target cells which express this antigen in an HLA-restricted manner, and also the autologous tumor cells, but not the autologous nontumor cells. They specifically secrete IFNγ after restimulation by means of cells presenting the peptide for which they are specific in the correct HLA context.

The invention claimed is:

1. A method for inducing and amplifying antigen specific effectors in vitro, which comprises the following steps:
  (a) obtaining pulsed plasmacytoid dendritic cells (pDCs) by incubation of a pDC line with at least one antigen,
  (b) irradiating the cells obtained in (a),
  (c) obtaining purified-peripheral blood mononuclear cells (PBMCs) from an individual, said PBMCs sharing at least one major histocompatibility complex (MHC) allele with the pulsed and irradiated pDCs obtained in step (b), and
  (d) bringing the pulsed and irradiated pDCs obtained in step (b) into contact with the PBMCs obtained in step (c) and culturing said pulsed and irradiated pDCs with said PBMCs; and thereby inducing and amplifying antigen specific effectors in the culture in vitro, wherein the antigen specific effectors are CD8+ T lymphocytes.

2. The method for inducing and amplifying antigen specific effectors of claim 1, which comprises at least one restimulation step consisting of
  (e) bringing the cells obtained in step (d) into contact again with the pulsed and irradiated pDC line obtained in step (b), and culturing.

3. A method for inducing and amplifying antigen specific effectors in an individual in need thereof, which comprises the following steps:
  (a) obtaining pulsed pDCs cells sharing at least one MHC allele with the PBMCs of said individual by incubation of a pDC line with at least one antigen,
  (b) irradiating the cells obtained in step (a),
  (c) injecting the pulsed and irradiated pDC cells obtained in step (b) into said individual,
  the pDCs cells sharing at least one MHC allele with the PBMCs of said individual into which they are injected, and thereby inducing and amplifying antigen specific effectors in said individual, wherein the antigen specific effectors are CD8+ T lymphocytes.

4. The method for inducing and amplifying antigen specific effectors as claimed in claim 3, in which the injection of the pulsed, irradiated pDCs of step (b) is repeated at least once.

5. The method for inducing and amplifying antigen specific effectors as claimed in claim 1, wherein the at least one antigen is a tumor antigen, a microbial antigen, or a viral antigen.

6. The method for inducing and amplifying antigen specific effectors as claimed in claim 5, wherein the antigen is a peptide.

7. The method for inducing and amplifying antigen specific effectors as claimed in claim 6, wherein the peptide is chosen from the peptides included in the sequence of the tumor antigens CEA, NY-BR1, Her-2/Neu, PSA, RAGE-1, PRAME, TRP-2, MAGE-A1, MAGE-A2, MAGE-A4, MAGE-A9, MAGE-A10, MAGE-C2, MUC-1, p53, hTERT, survivin, melan-A/MART-1, GP100, tyrosinase, MAGE-A3 or NY-ESO1.

8. The method for inducing and amplifying antigen specific effectors as claimed in claim 6, wherein the peptide is chosen from the peptides included in the sequence of the viral antigens env, nef, gp41, gp120, gag or pol of the HIV virus, HBc or HBs of the HBV virus, core, NS3 or NS5 of the HCV virus, Flu M1 of the influenza virus, pp65 of the CMV virus, BMLF1, LMP2, EBNA-2 or EBNA-3a of the EBV virus.

9. The method for inducing and amplifying antigen specific effectors as claimed in claim 1, wherein the pDC line is obtained from pDC leukemia cells.

10. The method for inducing and amplifying antigen specific effectors as claimed in claim 9, wherein the pDC line is the GEN2.2 line or the GEN3 line.

11. A method for treating cancers and/or infectious diseases, comprising
  (a) obtaining pulsed plasmacytoid dendritic cells (pDCs) by incubation of a pDC line with at least one antigen, (b) irradiating the cells obtained in (a),
(c) obtaining purified-peripheral blood mononuclear cells (PBMCs) from an individual in need of such treatment, wherein the PBMCs share at least one major histocompatibility complex (MHC) allele with the pulsed and irradiated pDCs obtained in step (b), and
(d) bringing the pulsed and irradiated pDCs obtained in step (b) into contact with the PBMCs obtained in step (c) and culturing said pulsed and irradiated pDCs with said PBMCs; and thereby inducing and amplifying antigen specific effectors in the culture in vitro, wherein the antigen specific effectors are CD8+ T lymphocytes; and
(e) injecting the antigen specific effectors into the individual in need of such treatment.

12. The method for inducing and amplifying antigen-specific effectors as claimed in claim 1, which further comprises a step (e) consisting of:
(e) collecting the antigen-specific effectors induced and amplified in step (d).

13. The method of claim 11, wherein the at least one antigen a tumor antigen, a microbial antigen, or a viral antigen.

14. The method of claim 11, wherein the at least one antigen is a peptide included in the sequence of the antigens CEA, NY-BR1, Her-2/Neu, PSA, RAGE-1, PRAME, TRP-2, MAGE-A1, MAGE-A2, MAGE-A4, MAGE-A9, MAGE-A10, MAGE-C2, MUC-1, p53, hTERT, survivin, melan-A/MART-1, GP100, tyrosinase, MAGE-A3 or NY-ESO1.

15. The method of claim 11, wherein the at least one antigen is a peptide included in the sequence of the antigens env, nef, gp41, gp120, gag or pol of the HIV virus, HBc or HBs of the HBV virus, core, NS3 or NS5 of the HCV virus, Flu M1 of the influenza virus, pp65 of the CMV virus, BMLF1, LMP2, EBNA-2 or EBNA-3a of the EBV virus.

16. The method for inducing and amplifying antigen specific effectors as claimed in claim 3, wherein the at least one antigen is a tumor antigen, a microbial antigen, or a viral antigen.

17. The method for inducing and amplifying antigen specific effectors as claimed in claim 16, wherein the antigen is a peptide.

18. The method for inducing and amplifying antigen specific effectors as claimed in claim 17, wherein the peptide is chosen from a peptide included in the sequence of tumor antigens CEA, NY-BR1, Her-2/Neu, PSA, RAGE-1, PRAME, TRP-2, MAGE-A1, MAGE-A2, MAGE-A4, MAGE-A9, MAGE-A10, MAGE-C2, MUC-1, p53, hTERT, survivin, melan-A/MART-1, GP100, tyrosinase, MAGE-A3 or NY-ESO1.

19. The method for inducing and amplifying antigen specific effectors as claimed in claim 17, wherein the peptide is chosen from a peptide included in the sequence of viral antigens env, nef, gp41, gp120, gag or pol of the HIV virus, HBc or HBs of the HBV virus, core, NS3 or NS5 of the HCV virus, Flu M1 of the influenza virus, pp65 of the CMV virus, BMLF1, LMP2, EBNA-2 or EBNA-3a of the EBV virus.

20. The method for inducing and amplifying antigen specific effectors as claimed in claim 3, wherein the pDC line is obtained from pDC leukemia cells.

21. The method for inducing and amplifying antigen specific effectors as claimed in claim 20, wherein the pDC line is the GEN2.2 line or the GEN3 line.

* * * * *

SEQUENCE LISTING

```
<160> NUMBER OF SEQ ID NOS: 13

<210> SEQ ID NO 1
<211> LENGTH: 10
<212> TYPE: PRT
<213> ORGANISM: Homo sapiens

<400> SEQUENCE: 1

Glu Leu Ala Gly Ile Gly Ile Leu Thr Val
1               5                   10

<210> SEQ ID NO 2
<211> LENGTH: 9
<212> TYPE: PRT
<213> ORGANISM: Homo sapiens

<400> SEQUENCE: 2

Ile Met Asp Gln Val Pro Phe Ser Val
1               5

<210> SEQ ID NO 3
<211> LENGTH: 9
<212> TYPE: PRT
<213> ORGANISM: Homo sapiens

<400> SEQUENCE: 3

Tyr Met Asp Gly Thr Met Ser Gln Val
1               5
```

-continued

```
<210> SEQ ID NO 4
<211> LENGTH: 9
<212> TYPE: PRT
<213> ORGANISM: Homo sapiens

<400> SEQUENCE: 4

Phe Leu Trp Gly Pro Arg Ala Leu Val
1               5

<210> SEQ ID NO 5
<211> LENGTH: 9
<212> TYPE: PRT
<213> ORGANISM: Homo sapiens

<400> SEQUENCE: 5

Ser Leu Leu Met Trp Ile Thr Gln Cys
1               5

<210> SEQ ID NO 6
<211> LENGTH: 9
<212> TYPE: PRT
<213> ORGANISM: Human Immunodeficiency virus (HIV)

<400> SEQUENCE: 6

Ser Leu Tyr Asn Thr Val Ala Thr Leu
1               5

<210> SEQ ID NO 7
<211> LENGTH: 9
<212> TYPE: PRT
<213> ORGANISM: Human Immunodeficiency virus (HIV)

<400> SEQUENCE: 7

Ile Leu Lys Glu Pro Val His Gly Val
1               5

<210> SEQ ID NO 8
<211> LENGTH: 9
<212> TYPE: PRT
<213> ORGANISM: Influenza Virus

<400> SEQUENCE: 8

Gly Ile Leu Gly Phe Val Phe Thr Leu
1               5

<210> SEQ ID NO 9
<211> LENGTH: 9
<212> TYPE: PRT
<213> ORGANISM: Cytomegalovirus (CMV)

<400> SEQUENCE: 9

Asn Leu Val Pro Met Val Ala Thr Val
1               5

<210> SEQ ID NO 10
<211> LENGTH: 9
<212> TYPE: PRT
<213> ORGANISM: Epstein Barr Virus

<400> SEQUENCE: 10

Gly Leu Cys Thr Leu Val Ala Met Leu
1               5
```

```
<210> SEQ ID NO 11
<211> LENGTH: 9
<212> TYPE: PRT
<213> ORGANISM: Epstein Barr Virus

<400> SEQUENCE: 11

Cys Leu Gly Gly Leu Leu Thr Met Val
1               5

<210> SEQ ID NO 12
<211> LENGTH: 10
<212> TYPE: PRT
<213> ORGANISM: Epstein Barr Virus

<400> SEQUENCE: 12

Asp Thr Pro Leu Ile Pro Leu Thr Ile Phe
1               5                   10

<210> SEQ ID NO 13
<211> LENGTH: 9
<212> TYPE: PRT
<213> ORGANISM: Epstein Barr Virus

<400> SEQUENCE: 13

Ser Val Arg Asp Arg Leu Ala Arg Leu
1               5
```